(12) United States Patent
Tarasov et al.

(10) Patent No.: US 12,241,859 B2
(45) Date of Patent: Mar. 4, 2025

(54) POLYMER-COATING OF ELECTRODES FOR SENSOR DEVICES

(71) Applicant: Roche Diagnostics Operations, Inc., Indianapolis, IN (US)

(72) Inventors: Alexey Tarasov, Neckargemuend (DE); Nesha Andoy, Heidelberg (DE); Marcin Filipiak, Dossenheim (DE); Oscar Gutierrez-Sanz, Heidelberg (DE); Natalie Haustein, Dossenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 645 days.

(21) Appl. No.: 16/546,452

(22) Filed: Aug. 21, 2019

(65) Prior Publication Data
US 2020/0033291 A1 Jan. 30, 2020

Related U.S. Application Data

(63) Continuation of application No. PCT/EP2018/054280, filed on Feb. 21, 2018.

(30) Foreign Application Priority Data

Feb. 22, 2017 (EP) ..................................... 17157373

(51) Int. Cl.
*G01N 27/414* (2006.01)
*G01N 33/543* (2006.01)

(52) U.S. Cl.
CPC ..... *G01N 27/4145* (2013.01); *G01N 33/5438* (2013.01)

(58) Field of Classification Search
CPC ........... G01N 27/4145; G01N 33/5438; G01N 27/4146; G01N 33/573; G01N 33/551; G01N 33/48721; B81C 1/0206
USPC .................. 436/512, 516; 257/27, 205, 49; 422/82.03, 82.01; 326/49, 68; 427/2.13, 427/338; 204/403.01

See application file for complete search history.

(56) References Cited

U.S. PATENT DOCUMENTS

| 7,332,327 | B2 * | 2/2008 | Vikholm | .......... | G01N 33/54393 436/805 |
| 8,524,057 | B2 | 9/2013 | Rothberg et al. | | |
| 2006/0102471 | A1 * | 5/2006 | Maurer | ..................... | C25F 1/00 204/290.01 |
| 2006/0141485 | A1 * | 6/2006 | Su | ........................ | C12Q 1/6837 435/7.1 |
| 2009/0170982 | A1 | 7/2009 | Dupont | | |
| 2015/0122646 | A1 | 5/2015 | Al-Rubeaan et al. | | |
| 2017/0105119 | A1 | 4/2017 | Babbage et al. | | |

FOREIGN PATENT DOCUMENTS

| CN | 1875113 | A | 12/2006 | | |
| CN | 101331274 | A | 12/2008 | | |
| CN | 102203282 | A | 9/2011 | | |
| CN | 104487565 | A | 4/2015 | | |
| JP | 2009-139113 | A | 6/2009 | | |
| JP | 2016-038384 | B2 | 3/2016 | | |
| WO | 2015192064 | A1 | 12/2015 | | |
| WO | WO-2016161246 | A1 | * 10/2016 | ......... | G01N 27/4145 |
| WO | 2017026901 | A1 | 2/2017 | | |

OTHER PUBLICATIONS

Park KD, Kim YS, Han DK, Kim YH, Lee EH, Suh H, Choi KS. Bacterial adhesion on PEG modified polyurethane surfaces. Biomaterials. Apr.-May 1998;19(7-9):851-9. doi: 10.1016/s0142-9612(97)00245-7. PMID: 9663762 (Year: 1998).*

Tarasov et al., "Gold-coated graphene field-effect transistors for quantitative analysis of protein-antibody interactions," 2D Mater., 2015, vol. 2, No. 4, pp. 1-7.*

Yoshimoto et al., "Direct observation of adsorption-induced inactivation of antibody fragments surrounded by mixed-PEG layer on a gold surface," J. Am. Chem. Soc., 2010, vol. 132, No. 23, pp. 7982-7989.*

Gutiérrez-Sanz et al., "Direct, Label-Free, and Rapid Transistor-Based Immunodetection in Whole Serum," ACS Sens., 2017, vol. 2, No. 9, pp. 1278-1286; Publication Date: Aug. 30, 2017.*

Girish et al., Detection beyond the Debye Screening Length in a High-Frequency Nanoelectronic Biosensor; NANO Letters; 2012, vol. 12, pp. 719-723.

Nassef et al., Amperometric Immunosensor for Detection of Celiac Disease Toxic Gliadin on Fab Fragments; Anal. Chem., 2009, vol. 81, pp. 5299-5307.

Elnathan et al., Biorognition Layer Engineering: Overcoming Screening Limitations of Nanowire-Based FET Devices; NANO Letters, 2012, vol. 12, pp. 5245-5254.

Rother et al., Understanding Charge Transport in Mixed Networks of Semiconducting Carbon Nanotubes; Applied Materials & Interfaces; 2016, vol. 8, pp. 5571-5579.

(Continued)

*Primary Examiner* — Galina M. Yakovleva
(74) *Attorney, Agent, or Firm* — Taft Stettinius & Hollister LLP

(57) ABSTRACT

An electrode comprising a functionalized surface exposable to a fluid sample. The functionalized surface comprises at least one polymer capable of mediating a salting-out effect and at least one detection agent that binds to an analyte comprised in the fluid sample, wherein the polymer and the detection agent are distributed on the surface of the electrode such that the detection agent is present in essentially equal amounts per surface area throughout the electrode surface and the polymer is arranged around the detection agent present in an amount allowing the reduction of the ionic strength of the fluid in proximity to the detection agent, and allowing for binding an analyte comprised in the fluid sample. A method for manufacturing a functionalized surface on an electrode, an analyte detector comprising the electrode, and the use of the analyte detector for determining at least one analyte in a fluid sample are also provided.

3 Claims, 15 Drawing Sheets

Specification includes a Sequence Listing.

(56) References Cited

OTHER PUBLICATIONS

Shim et al., Funtionalization of Carbon Nanotubes for Biocompatibility and Biomolecular Recognition; American Chemical Society; 2002, vol. 2, No. 4, pp. 285-288.

Elnathan, Roey et al., Biorecognition Layer Engineering: Overcoming Screening Limitations of Nanowire-Based FET Devices, Nano Letters, 2012, pp. 5245-5254, vol. 12.

Gao, Ning et al., General Strategy for Biodetection in High Ionic Strength Solutions Using Transistor-Based Nanoelectronic Sensors, Nano Letters, 2015, pp. 2143-2148, vol. 15.

Gao, Ning et al., Specific detection of biomolecules in physiological solutions using graphene transistor biosensors, PNAS, 2016, pp. 14633-14638, vol. 113, No. 51.

International Search Report issued May 16, 2018, in Application No. PCT/EP2018/054280, 4 pp.

Kulkarni, Girish S. and Zhong, Zhaohui, Detection beyond the Debye Screening Length in a High-Frequency Nanoelectronic Biosensor, Nano Letters, 2012, pp. 719-723, vol. 12.

Magliulo, Maria et al., Label-free C-reactive protein electronic detection with an electrolyte-gated organic field-effect transistor-based immunosensor, Analytical and Bioanalytical Chemistry, 2016, pp. 3943-3952, vol. 408.

Nassef, Hossam M. et al., Amperometric Immunosensor for Detection of Celiac Disease Toxic Gliadin Based on Fab Fragments, Analytical Chemistry, 2009, pp. 5299-5307, vol. 81, No. 13.

Rother, Marcel et al., Understanding Charge Transport in Mixed Networks of Semiconducting Carbon Nanotubes, ACS Applied Materials & Interfaces, 2016, pp. 5571-5579, vol. 8.

Shim, Moonsub et al., Functionalization of Carbon Nanotubes for Biocompatibility and Biomolecular Recognition, Nano Letters, 2002, pp. 285-288, vol. 2, No. 4.

Tarasov, Alexey et al., A potentiometric biosensor for rapid on-site disease diagnostics, Biosensors and Bioelectronics, 2016, pp. 669-678, vol. 79.

Tarasov, Alexey et al., Gold-coated graphene field-effect transistors for quantitative analysis of protein-antibody interactions, 2D Materials, 2015, 8 pp., vol. 2, Article 044008.

Tarasov, Alexey et al., Understanding the Electrolyte Background for Biochemical Sensing with Ion-Sensitive Field-Effect Transistors, ACS Nano, 2012, pp. 9291-9298, vol. 6, No. 10.

Yoshimoto, Keitaro et al., Direct Observation of Adsorption-Induced Inactivation of Antibody Fragments Surrounded by Mixed-PEG Layer on a Gold Surface, Journal of the American Chemical Society, 2009, pp. 7982-7989, vol. 132.

\* cited by examiner

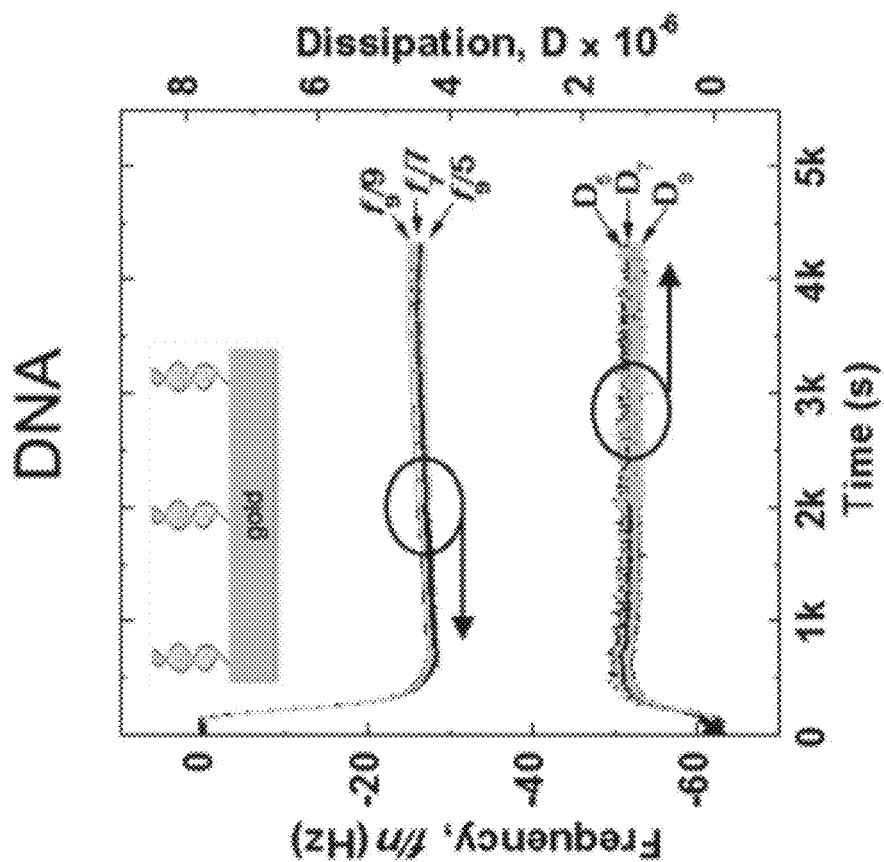
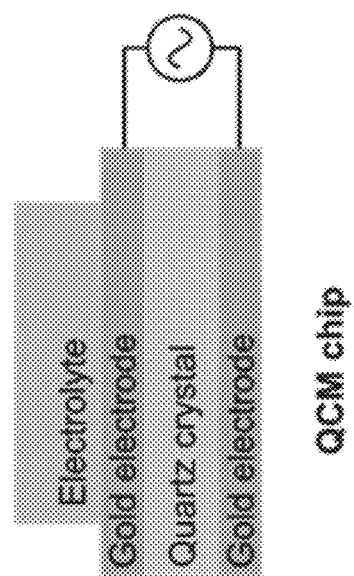
Fig. 1B
Fig. 1A

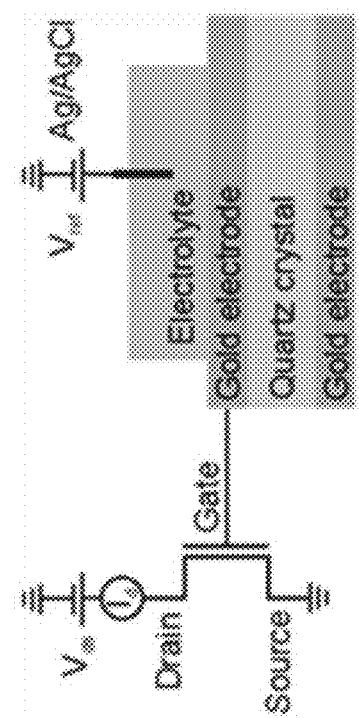
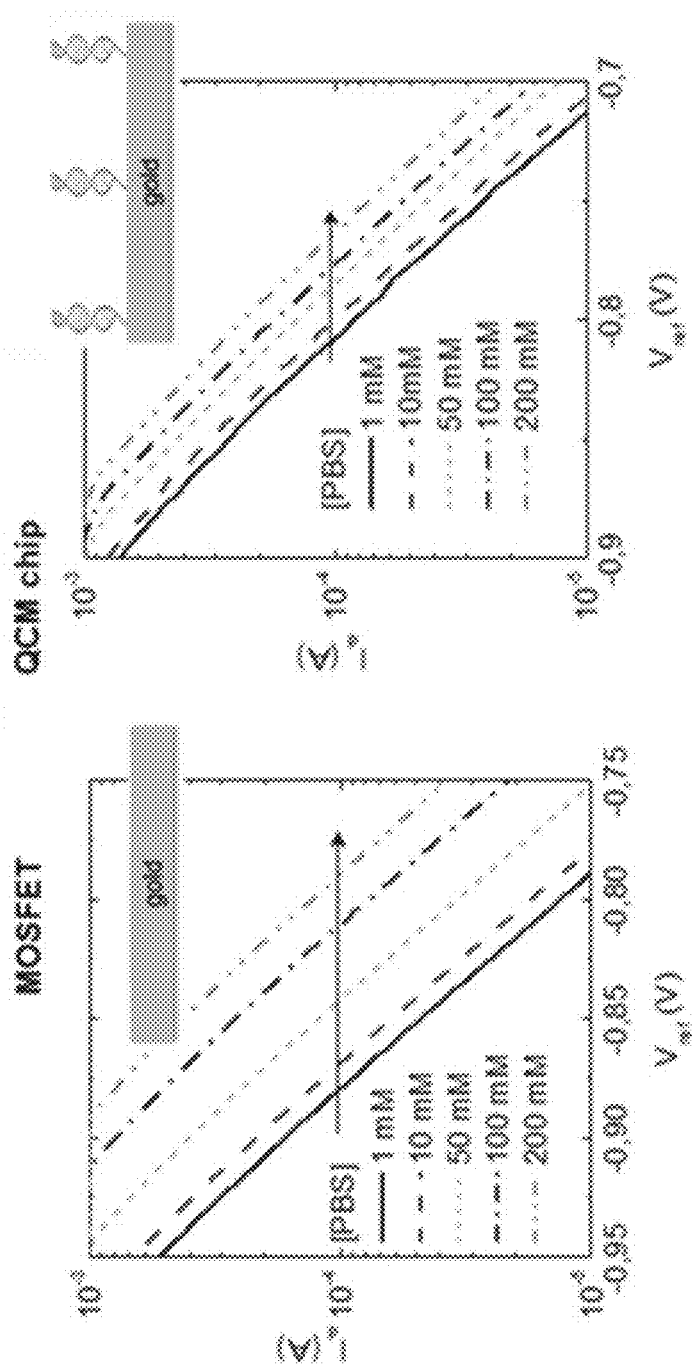
Fig. 2A
Fig. 2B
Fig. 2C

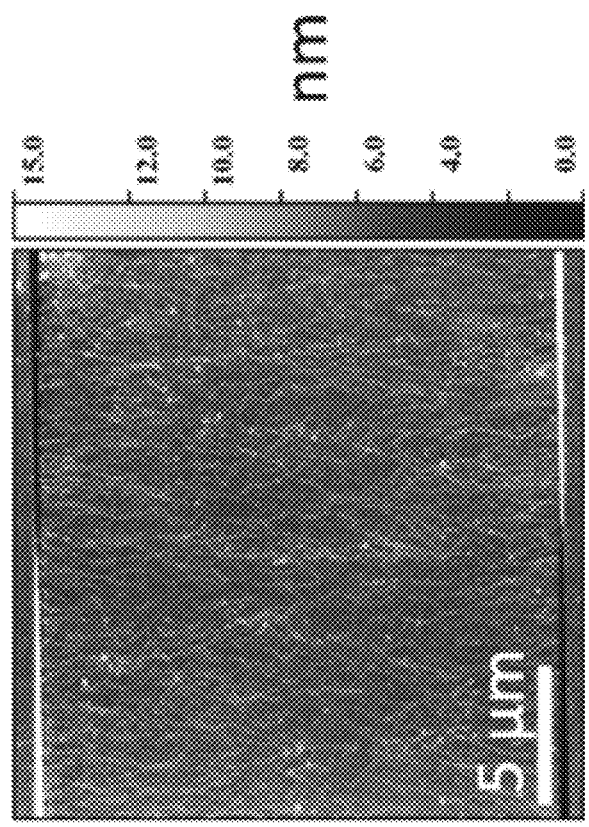
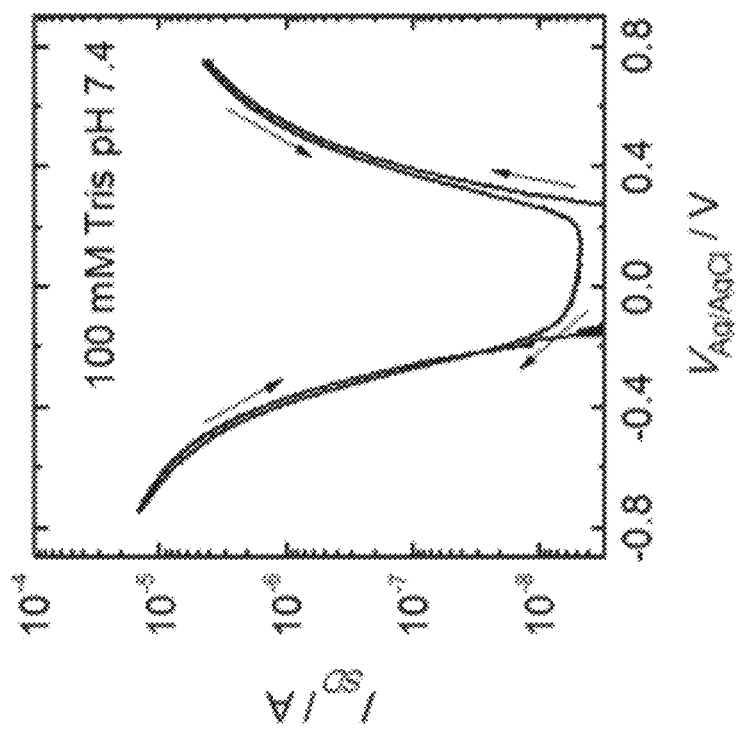
Fig. 4C
Fig. 4D

POLYMER-COATING OF ELECTRODES FOR SENSOR DEVICES

CROSS-REFERENCE TO RELATED APPLICATIONS

This application is a continuation of International Patent Application No. PCT/EP2018/054280, filed 21 Feb. 2018, which claims the benefit of European Patent Application No. 17157373.6, filed 22 Feb. 2017, the disclosures of which are hereby incorporated herein by reference in their entirety.

INCORPORATION OF SEQUENCE LISTING

A paper copy of the Sequence Listing and a computer readable form of the Sequence Listing containing the file named "P33974-US-cps_ST25.txt", which is 777 bytes in size (as measured in MICROSOFT WINDOWS EXPLORER®), are provided herein and are herein incorporated by reference. This Sequence Listing consists of SEQ ID NOS:1-2.

TECHNICAL FIELD

The present disclosure concerns the field of sensor equipment for analyzing samples using electrochemical or electrical field-effect based detection methods. In particular, the present disclosure relates to an electrode comprising a functionalized surface exposable to a fluid sample, said functionalized surface comprises at least one polymer capable of mediating a salting-out effect and at least one detection agent that binds to an analyte comprised in the fluid sample, wherein the said at least one polymer capable of mediating a salting-out effect and the said at least one detection agent are distributed on the surface of the electrode such that the detection agent is present in essentially equal amounts per surface area throughout the electrode surface and the polymer capable of mediating a salting-out effect is arranged around the detection agent present in an amount allowing the reduction of the ionic strength of the fluid in proximity to the detection agent, and allowing for binding an analyte comprised in the fluid sample. The disclosure further relates to a method for manufacturing a functionalized surface on an electrode, to an analyte detector for determining at least one analyte comprising the electrode, and to the use of the said analyte detector for determining at least one analyte in a fluid sample.

BACKGROUND

In recent years there has been great progress in applying field-effect-transistor (FET)-based sensors for biological detection. FET-based measurements require binding of a charged molecule to the sensor surface, changing its surface potential, and consequently changing the channel current inside the transistor. This charged-based sensing mechanism renders FET measurements label-free and highly sensitive for a wide range of biological targets. For example, FET-biosensors have been applied to detect a variety of biomolecules such as nucleic acids (DNA and RNA), enzymes, protein disease markers, and even whole viruses, bacteria, and eukaryotic cells. Due to their versatility, high sensitivity and fast response, FET-based biosensors are well positioned to find applications in Point-of-Care (PoC) devices.

Notwithstanding the above mentioned advantages, FET-based bio-sensing has been limited to date with measurements in low ionic strength solutions. This is because detecting charges in high ionic strength environments is impeded by Debye screening, where charged molecules in ionic solutions attract counter-ions forming an electric double layer that effectively screens off the charges on the molecule, i.e., negatively charged molecules like DNA will be surrounded by cations via electrostatic interactions. Debye screening is therefore dependent on the electrolyte concentration.

Under physiological conditions, where ionic strength is >100 mM, the Debye screening effect limits detection to within about 1 nm from the sensor surface. For this reason, most FET-based biosensors have only been operated under non-physiological ionic strength conditions, either by pre-desalting or diluting the sample. In order to be applicable in PoC settings, the ionic screening has to be reduced in a more direct and efficient way as sample processing capabilities are very limited at near-patient sites.

A couple of recent studies have reported several strategies to mitigate this Debye screening problem. The use of smaller receptors, e.g., aptamers or smaller antibody fragments, to bring the target molecule closer to the electrode surface has been reported to enhance transistor-based detection of proteins. In addition, it has been demonstrated that by operating a high frequency FET measurement, the ionic screening effect can be mitigated.

More recently, it has been shown that the co-immobilization of polyethylene glycol (PEG) on the sensor enables transistor-based detection of biomolecules in high ionic strength solutions.

PEGs were also described on electrode materials for different purposes. For example, they were described as linkers for probe immobilization and for reducing unspecific binding. Further, PEG may act as a stabilizer for Fab fragments.

BRIEF SUMMARY

It is against the above background that the embodiments of the present disclosure provide certain unobvious advantages and advancements over the prior art. In particular, the inventors have recognized a need for improvements in polymer-coating of electrodes for sensor devices.

In accordance with one embodiment of the present disclosure, a method for manufacturing a functionalized surface on an electrode is provided comprising the steps of: a) applying to the electrode a linker and at least one polymer capable of mediating a salting-out effect under conditions which allow for covalent or non-covalent immobilization of the said linker and the said polymer on the surface of the electrode; and b) applying at least one detection agent to the electrode upon immobilization of the said linker and the said polymer under conditions which allow for covalent or non-covalent attachment of the said at least one detection molecule to the electrode via the immobilized linker; and wherein the conditions allow for distributing the said at least one polymer capable of mediating a salting-out effect and the said at least one detection agent on the surface of the electrode such that the detection agent is present in equal amounts per surface area throughout the electrode surface and the polymer capable of mediating a salting-out effect is arranged around the detection agent present in an amount i) allowing the reduction of the ionic strength of a fluid in proximity to the detection agent, and ii) allowing for binding an analyte comprised in a fluid sample.

In accordance with another embodiment of the present disclosure, an electrode comprising a functionalized surface exposable to a fluid sample is provided, said functionalized surface comprises at least one polymer capable of mediating a salting-out effect and at least one detection agent that binds to an analyte comprised in the fluid sample, wherein the said at least one polymer capable of mediating a salting-out effect and the said at least one detection agent are distributed on the surface of the electrode such that the detection agent is present in essentially equal amounts per surface area throughout the electrode surface and the polymer capable of mediating a salting-out effect is arranged around the detection agent present in an amount i) allowing the reduction of the ionic strength of the fluid in proximity to the detection agent, and ii) allowing for binding an analyte comprised in the fluid sample.

In accordance with yet another embodiment of the present disclosure, a method for determining at least one analyte is provided comprising the steps of: (a) contacting a fluid sample suspected to comprise the at least one analyte to the electrode of the present disclosure; and (b) performing an electrochemical measurement with said electrode or detector, whereby the at least one analyte will be determined.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIGS. 1A-1F show surface characterization by Quartz Crystal Microbalance. FIG. 1A is a schematic of the QCM chip. FIGS. 1B-1D show a representative data set illustrating typical frequency and dissipation changes vs. time for different overtones (n=5, 7, 9) and surface modifications: dsDNA (FIG. 1B), PEG (FIG. 1C), and mix of both (FIG. 1D). In general, the frequency decreases upon adsorption of molecules while the dissipation increases. FIGS. 1E and 1F show a summary of the dissipation and frequency changes obtained from at least 3 chips. The dissipation increase is more than 3× stronger for PEG because it is softer than DNA (FIG. 1E). This is also seen as "spreading" of overtones for the PEG-modified surface (FIG. 1F).

FIGS. 2A-2E show FET measurements. FIG. 2A is a schematic of the extended-gate FET configuration, with the gold surface of the QCM chip connected to a spatially separated commercial MOSFET. FIGS. 2B-2D show typical transfer curves recorded in different concentrations of PBS buffer using different surfaces: bare gold (FIG. 2B), dsDNA (FIG. 2C), and DNA+PEG mix (FIG. 2E). FIG. 2D shows potential changes vs. PBS concentration for 3 different surfaces. Delta V becomes more positive for gold due to non-specific ion adsorption (background). With DNA on the surface, the effect of DNA screening is superimposed resulting in a less pronounced shift to positive values. The opposite trend is observed for the mix layer.

FIGS. 4A-4D show schematics of the measurement setup. The semiconducting CNT (carbon nanotube) network is aligned between interdigitated Au electrodes (channel length=20 μm, channel width=2 mm). Additionally, the contacts are passivated with SU-8 photoresist to avoid leakage current. SU-8 is a negative, epoxy-type, near-UV photoresist based on EPON SU-8 epoxy resin (from Shell Chemical) that has been originally developed, and patented (U.S. Pat. No. 4,882,245) by IBM. To provide different liquids to the sensing surface, a microfluidic PDMS chamber with PTFE tubing was used. The Ag/AgCl reference electrode is placed in the middle of microfluidic channel. FIG. 4B is a photo of the measurement setup. FIG. 4C shows typical transfer curves in both polarization directions. The hysteresis is very small. FIG. 4D shows an AFM image of the electric field aligned CNT network. Horizontal stripes on the top and bottom are gold electrodes used to align CNTs. The same electrodes were later used as source and drain contacts for electrical measurements.

FIGS. 5B and 5E show the transfer curves measured in different concentrations of GFP in 100 mM Tris buffer. A shift to the right is visible in both cases with a stronger response in the PEGylated case (FIG. 5B). FIGS. 5C and 5F summarize the potential shift ΔV obtained as a function of GFP concentration CGFP in 1 mM and 100 mM ionic strength solutions. ΔV was read out at a constant $I_{SD}$ value, as indicated by horizontal lines in FIGS. 5B and 5E. The signal in FIG. 5C is up to 3× larger than the signal in FIG. 5F, which is attributed to the local buffer dilution by PEG.

Figure 1D:
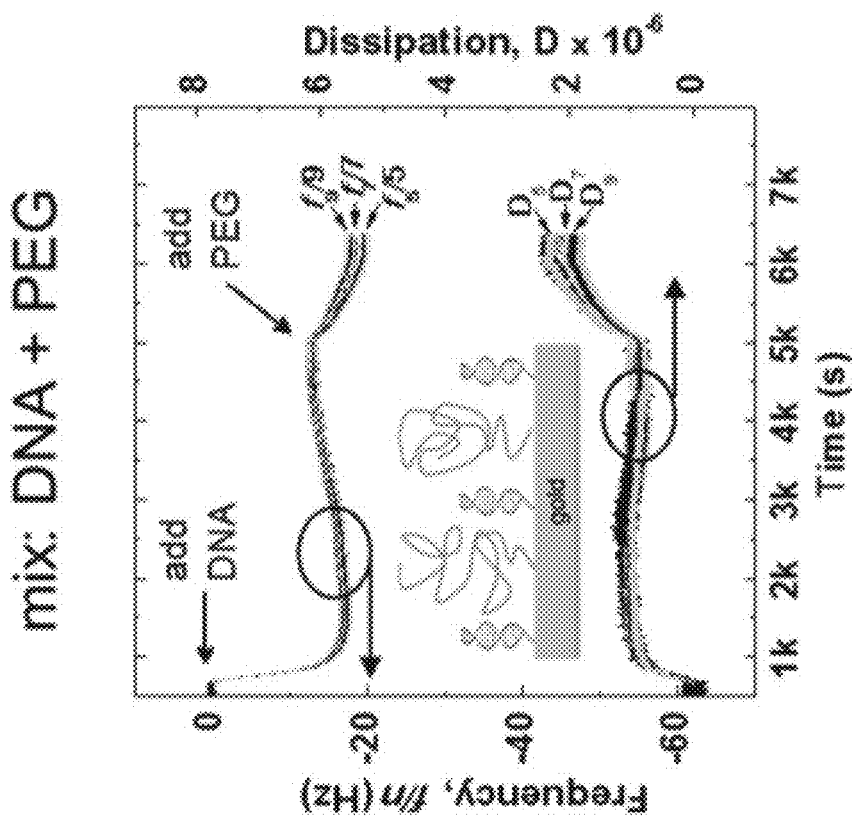

Skilled artisans appreciate that elements in the figures are illustrated for simplicity and clarity and have not necessarily been drawn to scale. For example, dimensions of some of the elements in the figures may be exaggerated relative to other elements to help improve understanding of the embodiments(s) of the present disclosure.

DETAILED DESCRIPTION

The present disclosure relates to an electrode comprising a functionalized surface exposable to a fluid sample, said functionalized surface comprises at least one polymer capable of mediating a salting-out effect and at least one detection agent that binds to an analyte comprised in the fluid sample, wherein the said at least polymer capable of mediating a salting-out effect and the said at least one detection agent are distributed on the surface of the electrode such that the detection agent is present in essentially equal amounts per surface area throughout the electrode surface and the polymer capable of mediating a salting-out effect is arranged around the detection agent and present in an amount i) allowing the reduction of the ionic strength of the fluid in proximity to the detection agent, and ii) allowing for binding an analyte comprised in the fluid sample.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once, i.e., two, three, four, five up to a non-limited number of times, typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically", "typically", "more typically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

The term "electrode" as used herein refers to a structure enabling electrical contact. The electrode is usually used for making an electrical contact with a non-metallic part of an electrical circuit, such as a semiconductor element, an electrolyte, a vacuum or air. Typically, an electrode comprises an electrically conducting material. In particular, the electrode to be used in accordance with the present disclosure is a solid support. As used herein, the term "electrode" may generally refer to a functional element configured to perform a current measurement and/or a voltage measurement and/or configured to apply a current and/or an electrical potential and/or a voltage to an element in electrical contact with the electrode. In particular, the electrode may comprise a conducting and/or a semiconducting material. As an example, the electrode may comprise at least one metallic material and/or at least one organic or inorganic semiconducting material, having at least one conducting or semiconducting surface. The surface itself may form the electrode or a part of the electrode. As an example, the electrode may comprise at least one material, specifically at least one surface material, having an electrical conductivity of at least 1000 S/m, e.g., at least 1000000 S/m, either isotropically or anisotropically in at least one direction. Specifically, the electrode may comprise graphene, carbon nanotubes, silicon nanowires, molybdenum oxide, molybdenum disulfide, titanium oxide, zinc oxide, a metal oxide, gallium nitride, gold, silicon, magnetic beads, nanoparticles or any combination of these materials.

The electrode is usually used for making an electrical contact with a non-metallic part of an electrical circuit, such as a semiconductor element, an electrolyte, a vacuum or air. Typically, an electrode comprises an electrically conducting material. In particular, the electrode to be used in accordance with the present disclosure is a solid support structure.

As used herein the term "in electrical contact" may generally refer to the arrangement or configuration of at least two components, wherein at least one of the components is able to electrically influence the at least one other component and/or to at least partially control an electrical quality of the other component such as, but not limited to, its conductivity and electrical current flow, for instance via electrostatic induction. In particular, an electrode may be in electrical contact with an element without being in direct physical contact with said element. Thus, an electrode may control the electrical current flow within an element by application of a voltage despite being insulated from said element. Insulation may, for instance, be constituted by an oxide layer as is typically the case for a gate electrode of a metal oxide semiconductor field-effect transistor (MOSFET) a subgroup of insulated-gate field-effect transistors (IGFET), which is described in more detail below. Thus, generally, for being in electrical contact with one another, the at least two components may be located in close proximity, without being in direct physical contact with one another, such that, however, the components may influence one another electrically. Additionally, or alternatively, however, the at least two components may also be physically connected via at least one connecting element having at least semiconducting properties or electrically conductive properties, such as by at least one electrical conductor. Again, additionally or alternatively, the at least two components may be separate components or may fully or partially be integrated into one another. As an example, the at least one electrode may either be connected to the field-effect transistor via at least one connecting element, such as via at least one electrically conductive lead, or may even fully or partially be integrated into the field-effect transistor.

The term "functionalized surface" as used herein refers to the surface of the electrode according to the present disclosure which has certain desired physical and/or chemical properties. The surface of the electrode according to the present disclosure shall be functionalized in that it comprises at least one polymer capable of mediating a salting-out effect and at least one detection agent that binds to an analyte comprised in the fluid sample. Moreover, the said polymer and detection agent shall be distributed on the surface of the electrode such that the detection agent is present in essentially equal amounts per surface area throughout the electrode surface. Moreover, in said arrangement the polymer capable of mediating a salting-out effect shall be present around the detection agent and be present in an amount that allows the reduction of the ionic strength of the fluid in proximity to the detection agent, and, simultaneously, allows for binding an analyte comprised in the fluid sample. The arrangement, typically, may be a continuous layer or may be a cluster arrangement, such as a spot-like arrangement around each detection agent.

The term "fluid sample" as used herein refers to any solution comprising an analyte to be detected or suspected to comprise such an analyte. The fluid sample may be an aqueous solution or may comprise other solvents including organic solvents. The fluid sample may be of any origin, e.g., it may be a fluid sample of a naturally occurring fluid including fluids present in the environment or fluids present in an organism (i.e., body fluids) or derived from an organism, such as extracts. Moreover, the fluid may be an artificial fluid, e.g., a fluid obtained by dissolving compounds to be analyzed in an appropriate solvent or a fluid obtained as a product of a chemical reaction. Typically, said fluid sample is a body fluid, a liquid or dissolved environmental sample or a solution of at least one chemical compound. More typically, said fluid is a high ionic strength fluid. The fluid sample, thus, shall comprise a high amount of cations and anions, e.g., arising from dissolved salts or buffers. Under high ionic strength, typically, it is to be understood that ions are present in a millimolar amount, typically, in an amount equal or larger than 10 mM, 25 mM, 50 mM, 75 mM, 100 mM, 150 mM or 200 mM. The body fluid is, typically, selected from the group consisting of: blood, plasma, serum or any fraction thereof, saliva, tears, mucus, lymph, cerebrospinal fluid, urine, feces, sweat, semen, synovial fluid.

The term "analyte" as used herein refers to a molecule which may or may not be present in the fluid sample and the presence of which and/or amount of which shall be detected. Depending on the kind of detection agent to be used, an analyte may be selected from various kinds of molecules. In particular, an analyte may be a small molecule, a peptide, a protein, an oligonucleotide, a polynucleotide, such as an RNA or a DNA, a polymer or other macromolecule, a virus or an organism such as a microorganism including unicellular organisms like bacteria, archaea, algae protozoa or fungi. Typically, however, analytes are small molecule compounds, such as substrates for enzymes of metabolic pathways, intermediates of such pathways or the products obtained by a metabolic pathway. Thus, more typically, the analyte in accordance with the present disclosure may be a metabolite. Metabolic pathways are well known in the art and may vary between species. Typically, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including, e.g., flavonoids and isoflavonoids), isoprenoids (including, e.g., terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are usually composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g., metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal.

The term "polymer capable of mediating a salting-out effect" as used herein refers to a macromolecule that comprises more than one monomer subunit. Usually, the monomer subunits of a polymer are chemically linked to each other whereby the macromolecule is formed. Polymers may consist of chemically identical monomers, i.e., be homopolymers, or may consist of chemically different monomers, i.e., be hetero-polymers. Due to its chemical architecture, polymers have various properties resulting from the monomer subunits and their properties as well as the macromolecular arrangement of said monomer subunits. The polymer envisaged in accordance with the present disclosure shall be capable of mediating a salting-out effect, i.e., it shall when arranged appropriately, e.g., as a layer, decrease the ionic strength of a surrounding ionic fluid within the said polymer layer. Usually, the polymer shall achieve this by enriching the solvent and, in particular, water molecules in its proximity while the ions are rejected from the surrounding of the polymer. As a consequence of the reduction of the ionic strength in a solvent in the areas surrounding the polymer, the electrostatic effect elicited by the dissolved ions will be reduced in proximity to the polymer molecules. Accordingly, if arranged appropriately, e.g., as a layer on an electrode, the Debye length between the analyte and the electrode in the fluid can be increased. The Debye length can be determined for an ionic solution by the following formula:

$$\lambda_D = \sqrt{\frac{\varepsilon_0 \varepsilon_r k_B T}{2 N_A e^2 I}}$$

wherein:
$\lambda_D$ is the Debye length;
$\varepsilon_0$ is the dielectric constant;
$\varepsilon_r$ is the permittivity of free space;
$k_B$ is the Boltzmann constant;
T is the temperature;
$N_A$ is the Avogadro number;
e is the elementary charge;
I is the ionic strength.

The ionic strength and the Debye length in a fluid can be determined by the skilled person without further ado. Further, the effect of a polymer on the Debye length can be determined by those skilled in the art by techniques well known in the art and described in the accompanying Examples below.

Typically, the size of the said at least one polymer capable of mediating a salting-out effect is such that the Debye length is increased and the ionic strength around the at least one detection molecule is reduced. More typically, the molecular weight (MW) of the said at least one polymer capable of mediating a salting-out effect is between 1 and 100 kDa, between 10 and 100 kDa, between 10 and 50 kDa, between 10 and 25 kDa, between 10 and 20 kDa or between 10 and 15 kDa.

Also typically, said at least one polymer capable of mediating a salting-out effect is selected from the group consisting of: poly(ethylene glycol) (PEG), poly(ethylene oxide), poly(propylene glycol), polyglycerol, polyacrylamide (PAM), polyethylineimine (PEI), polymethacrylate or another acrylic polymer, poly(vinyl alcohol) (PVA), poly (vinylpyrrolidone) (PVP), copolymers of the aforementioned polymers, polysaccharides, polypeptides, polynucleotides and polysiloxanes.

The aforementioned polymer capable of mediating a salting-out effect shall be immobilized on the surface of the electrode. Accordingly, the polymer may be linked directly or indirectly, i.e., via a linker, to the surface of the electrode. The kind of linkage used depends on the electrode material and the polymer. Thus, if chosen appropriately, a direct linkage between the polymer and the electrode surface can be achieved. However, the linkage, typically, will be indirect linkage via a linker. A linker as referred to in accordance with the present disclosure is a molecule and, more typically, a bifunctional molecule, which allows for direct binding both to the electrode surface and to the polymer. The binding as referred to herein may be covalent or non-covalent binding and, thus, may be permanent or reversible depending on the surrounding and conditions applied. The skilled person is well aware of how and under what conditions direct or indirect binding can be achieved and what type of linkers are suitable.

Typically, the polymer capable of mediating a salting-out effect is immobilized on the surface of the electrode via a linker or directly attached via a functional group without an additional linker. More typically, said linker is a linker having the following structure:

A-B—C wherein A is a first functional group from the classes: thiol, silane, phosphonic acid, aromatic molecules (e.g., pyrene), carboxyl, amine, NHS ester, maleimide, wherein B is a short organic chain from the following classes: low molecular weight polymer from the classes described above, hydrocarbons (e.g., alkyl, alkenyl, alkynyl, phenyl), oxygen containing groups (e.g., ether), haloalkanes (e.g., chloro), nitrogen containing groups (e.g., amide), sulfur containing groups (e.g., sulfoxide), phosphorus containing groups, boron containing groups, or a short inorganic polymer chain (e.g., Si-based (siloxane), P-based, B-based, S-based), and wherein C is a second functional group from the classes: carboxyl, amine, NHS ester, maleimide.

The term "detection agent" as used in accordance with the disclosure refers to a molecule which binds to an analyte to be detected when present in the fluid sample. Typically, the detection agent specifically and selectively binds to the said analyte, i.e., does not cross-react with other analytes which may or may not be present in the sample. Specific binding can be tested by various well known techniques. Depending on the type of analyte to be detected, the detection agent may be chosen from different classes of molecules. The skilled person is well aware of which type of analyte can be detected by what molecule used as detection agent. Typically, the detection agent is selected from the group consisting of: antibodies and fragments thereof, nucleic acids, aptamers, peptide nucleic acids (PNAs), receptor or ligand proteins or peptides, and enzymes.

Antibodies and fragments thereof as referred to herein encompass all types of antibodies which, typically, specifically bind to the analyte to be detected. Usually, the antibody according to the present disclosure is a monoclonal antibody, a polyclonal antibody, a single chain antibody, a chimeric antibody or any fragment or derivative of such antibodies being still capable of binding the analyte. Such fragments and derivatives comprised by the term antibody as used herein encompass a bispecific antibody, a synthetic antibody, a Fab, $F(ab)_2$, Fv or scFv fragment, or a chemically modified derivative of any of these antibodies. Antibodies or fragments thereof, in general, can be obtained by using methods well known in the art. Monoclonal antibodies can be prepared, e.g., by the techniques which comprise the fusion of mouse myeloma cells to spleen cells derived from immunized mammals and, typically, immunized mice according to the Köhler & Millstein technology.

Nucleic acids as referred to herein refer to all kinds of desoxyribonucleic acids (DNAs) and ribonucleic acids (RNAs) as well as chemically modified derivatives thereof. These molecules are well known in the art. Typically, nucleic acids as detection agents may be used to detect other nucleic acids as analytes. In such a case, the detection agent nucleic acids are partially or entirely complementary to the analyte nucleic acid to be detected or parts thereof. Typically, such nucleic acids may have the size of oligonucleotides, i.e., comprise between 5 and 35 nucleotides in length, more typically, between 10 and 25 nucleotides in length, or may be larger nucleic acid probes in the range of 100 to 1,000 nucleotides in length, more typically, between 300 and 600 nucleotides in length.

Aptamers as referred to in accordance with the present disclosure encompass nucleic acid and peptide aptamers. In addition to their ability to base pair, nucleic acids may also be used as aptamers to detect other analytes due to their capability of forming three dimensional structures which specifically bind to target molecules such as small molecules, proteins, nucleic acids, and even cells, tissues and organisms. Nucleic acid aptamers can be engineered through repeated rounds of in vitro selection or through the systematic evolution of ligands by exponential enrichment (SELEX) technology to bind to various molecular targets. Peptide aptamers are artificial peptides selected or engineered to bind specific target molecules. These peptides consist usually of one or more peptide loops of variable sequence displayed by a protein scaffold. They are typically isolated from combinatorial libraries and usually subsequently improved by directed mutation or rounds of variable region mutagenesis and selection.

Peptide nucleic acids (PNAs) are artificially synthesized polymers having a nucleic acid-like backbone composed of repeating N-(2-aminoethyl)-glycine units which are linked by peptide bonds. The various purine and pyrimidine bases are linked to the backbone by a methylene bridge and a carbonyl group. PNAs and nucleic acids have similar biological properties and, thus, PNAs may be used as detection agents like nucleic acids or aptamers.

A receptor or ligand protein or peptide in accordance with the present disclosure refers to a protein or a peptide which is capable of specifically recognizing other proteins or peptides. Typically, receptor and ligand peptides or proteins are capable of specifically interacting with other molecules such as other proteins or peptides. Therefore, receptors or ligands may be used as detection agents for such interacting proteins or peptides or even other molecules which interact therewith. It will be understood that in accordance with the present disclosure, a receptor or ligand protein or peptide may also encompass parts of entire biologically active receptors or ligands and, typically, parts encompassing the binding domains thereof. Receptor or ligand proteins and peptides may be naturally occurring receptors or artificially generated ones. Typical artificial peptides as detection agents also include cyclic peptides.

Also typically suitable as detection agents are enzymes. Enzymes are proteins or peptides which specifically bind to molecules (substrates) and which are capable of enzymatically converting said molecules into others (products). Accordingly, an enzyme is, typically, capable of specifically binding to a substrate and, thus, can be used for detecting such a substrate as an analyte being present in a fluid sample. Analytes recognized by enzymes usually comprise small molecules, peptides or proteins. However, some enzymes may also recognize macromolecules such as polymers. Suitable enzymes and their substrates are well known in the art.

Typically, said at least one detection agent is immobilized on the surface of the electrode via a linker. More typically, said linker is selected from the group consisting of: a low molecular weight (MW) polymer having a MW of between 0.01 to 5, between 0.01 to 1.0, between 0.01 to 0.5 or between 0.1 to 0.5 kDa, said polymer being, typically, selected from the group consisting of: poly(ethylene glycol) (PEG), poly(ethylene oxide), poly(propylene glycol), polyglycerol, polyacrylamide (PAM), polyethylineimine (PEI), polymethacrylate or another acrylic polymer, poly (vinyl alcohol) (PVA), poly(vinylpyrrolidone) (PVP) and a copolymer of the aforementioned polymers. Using such a low molecular weight polymer shall strengthen the conformational stability, flexibility and capability of binding of the detection agent to the analyte. It shall also reduce the non-specific adsorption of species other than the analyte. Alternatively, the linker used for the detection agent may also be a linker as described above for the polymer.

Particularly, it is envisaged in accordance with the present disclosure that the linker for the detection agent is a polymer as recited above. Moreover, it is particularly envisaged that the polymer capable of mediating a salting-out effect is of the same class of polymers as the linker polymer, i.e., both are a poly(ethylene glycol) (PEG), a poly(ethylene oxide), a poly(propylene glycol), a polyglycerol, a polyacrylamide (PAM), a polyethylineimine (PEI), a polymethacrylate or another acrylic polymer, a poly(vinyl alcohol) (PVA), a poly(vinylpyrrolidone) (PVP) or a copolymer of the aforementioned polymers. More typically, the linker polymer is a low molecular weight (MW) polymer having a MW of between 0.01 to 5, between 0.01 to 1.0, between 0.01 to 0.5 or between 0.1 to 0.5 kDa, whereas the molecular weight (MW) of the said at least one polymer capable of mediating a salting-out effect is between 1 and 100 kDa, between 10 and 100 kDa, between 10 and 50 kDa, between 10 and 25 kDa, between 10 and 20 kDa or between 10 and 15 kDa.

The polymer and detection agent shall be distributed on the surface of the electrode such that the detection agent is present in essentially equal amounts per surface area throughout the electrode surface. It will be understood that for the purpose of performing analyte detection measurements using the electrode of the disclosure, it is favorable that the detection agent is present homogeneously throughout the surface of the electrode. Such a homogenous presence can be achieved by applying the detection agent or the linker for the detection agent and the polymer as a homogenous solution to the surface of the electrode. Thereby, all areas of the electrode will statistically receive an essentially equal amount of the detection agent or the linker and the polymer. How such a homogenous coating can be achieved is also well established in the art and described herein elsewhere in more detail.

Moreover, the polymer shall be arranged around the detection agent and be present in an amount that allows the reduction of the ionic strength of the fluid in proximity to the detection agent, but still allows for binding an analyte comprised in the fluid sample. Typically, the detection agent is surrounded by polymer molecules such that the detection agent is not in free contact with the fluid sample. This allows that the polymer can reduce the ionic strength in the proximity to the detection agent such that the Debye length becomes increased. It will be understood that care should be taken that the size of the detection agent and the size of the polymer are such that the detection agent is within the polymer-layer or cluster on the surface and has no or only limited access to the free fluid sample. Accordingly, the size of the polymer shall be larger or equal to the size of the detection agent or, in other words, the detection agent shall be, typically, embedded in the polymer-layer or cluster. In the following table, detection agents and useful polymers for coating are listed:

TABLE 1

Polymers useful for individual detection agents

| Detection agent | Thickness of the polymer layer | Useful polymer |
| --- | --- | --- |
| dsDNA (size, e.g., 15 nt in length) | equal or larger than 5 nm | 5, 10, 20, 30, 40 kDa PEG |
| Nanobody | equal or larger than 4 nm | 5, 10, 20, 30, 40 kDa PEG |
| Antibody fragment Fab | equal or larger than 7 nm | 10, 20, 30, 40 kDa PEG |
| Antibody fragment F(ab)2 | equal or larger than 7 nm | 10, 20, 30, 40 kDa PEG |
| Monoclonal antibody | equal or larger than 15 nm | 20, 30, 40 kDa PEG |

The thickness of the polymer layer and the detection agent layer can be measured, calculated and/or predicted by techniques well known in the art. Thus, when considering the arrangement of polymer and detection agent as separate layers, based on the predictions and/or calculations polymers suitable in size can be selected for a given detection agent without further ado.

Moreover, a detection agent molecule shall be, typically, surrounded completely by polymer molecules on the surface. In order to achieve a proper arrangement for analyte detection, the said detection agent and/or the linker therefor are applied simultaneously with the said at least one polymer. Typically, the molar ratio of the at least one polymer capable of mediating a salting-out effect and the at least one detection agent present on the functionalized surface is between 1:100 to 100:1, 1:50 to 50:1, 1:20 to 20:1, 1:10 to 10:1, 1:5 to 5:1, 2:10 to 8:1, 3:10 to 7:1, 4:10 to 6:1 or 5:10 to 5:1. Such molar ratios allow for the formation of the aforementioned favorable arrangement of detection agents and polymers on the surface of the electrode. Particularly, a suitable layer or cluster arrangement of polymer and detection agent can be obtained by applying the polymer and the linker, typically, a polymer linker, as a solution in a suitable solvent to the electrode. Said solution, typically, comprises the polymer and the linker in a molecular weight ratio of 1:10 to 1:50, more typically, 1:20. It shall be understood that for larger detection agents, such as antibodies, receptors or enzymes, larger molecular ratios shall be used, i.e., the amount of the linker shall be increased.

Advantageously, in the studies underlying the present disclosure, the extent of the Debye length increase was quantified by systematically comparing double-stranded DNA (dsDNA) detection under different salt concentrations in the presence and absence of PEG. dsDNA is an ideal biomolecule to study Debye screening effects on FET-based measurements because of its uniform surface charge and easily tunable length. It was, inter alia, shown that PEG, immobilized together with dsDNA, can locally desalt the area immediately next to the sensor surface, lowering the local ionic strength at least 10×. This leads to the Debye screening effect being lowered in the vicinity surrounding the dsDNA molecules and allowing improved FET-based detection under physiological ionic strength solutions. Thus, it has been found in accordance with the present disclosure that surrounding detection agents on a surface of an electrode by polymers capable of mediating a salting-out effect allow for increasing the Debye length for electrode measurements. Accordingly, measurements can also be performed efficiently in solutions having a high ionic strength which normally prevents electrical field-effect based detection of analytes in such solutions. In particular, it has been found that the ionic strength of the solution is reduced in the polymer layer due to salting-out. However, the detection agents immobilized on the electrode must be surrounded in a spatial arrangement of polymer molecules which allows for binding of an analyte to the detection molecule and at the time for the said reduction of the ionic strength in the layer. A suitable arrangement of polymer and detection agent can be achieved by using a predefined mixture of detection agent or linkers for the detection agent and polymer molecules or linkers for said polymers. A process for the manufacturing of functionalized electrode surfaces is also provided thanks to the findings underlying the present disclosure and described in more detail elsewhere herein. Particularly advantageous shall be the use of a low molecular weight polymer as a linker for detection agents such as antibodies, peptides, receptors or enzymes since the conformational stability, flexibility and capability of binding to the analyte to the detection agent will be increased, and the non-specific adsorption of species other than the analyte reduced.

All definitions and explanations given for the terms above apply mutatis mutandis for all following embodiments.

The present disclosure further relates to a method for manufacturing a functionalized surface on an electrode comprising the steps of:
a) applying to the electrode a linker and at least one polymer capable of mediating a salting-out effect under conditions which allow for covalent or non-covalent immobilization of the said linker and the said polymer on the surface of the electrode; and
b) applying at least one detection agent to the electrode upon immobilization of the said linker and the said polymer under conditions which allow for covalent or non-covalent attachment of the said at least one detection molecule to the electrode via the immobilized linker; and
wherein the conditions allow for distributing the said at least one polymer capable of mediating a salting-out effect and the said at least one detection agent on the surface of the electrode such that the detection agent is present in equal amounts per surface area throughout the electrode surface and the polymer capable of mediating a salting-out effect is arranged around the detection agent present in an amount
i) allowing the reduction of the ionic strength of a fluid in proximity to the detection agent, and
ii) allowing for binding an analyte comprised in a fluid sample.

The linker and the at least one polymer capable of mediating a salting-out effect are applied to the electrode under conditions which allow for covalent or non-covalent immobilization of the said linker and the said polymer on the surface of the electrode. Accordingly, depending on the kind of immobilization of said molecules, the molecules may be covalently linked to the electrode surface or adhere by non-covalent mechanisms. Typically, covalent binding of a linker or the polymer can be achieved by functional groups present in the linker or polymer molecules. Said functional groups are capable of forming covalent bounds to the electrode surface. Said functional groups may also be present in the polymers in order to allow for covalent linkage thereof to the electrode. Typically, non-covalent binding of a linker or the polymer can be also achieved by functional groups present in the linker or polymer molecules. Said functional groups are capable of forming non-covalent bounds to the electrode surface, e.g., via electrostatic interactions, hydrophobic interactions, pi-interactions, hydrogen bonds or Van-der-Waals forces. Typical functional groups may be thiol, silane, phosphonic acid, aromatic molecules (e.g., pyrene), carboxyl, amine, NHS ester, maleimide.

Also typically, said at least one polymer capable of mediating a salting-out effect to be used in the method of the present disclosure is selected from the group consisting of: poly(ethylene glycol) (PEG), poly(ethylene oxide), poly (propylene glycol), polyglycerol, polyacrylamide (PAM), polyethylineimine (PEI), polymethacrylate or another acrylic polymer, poly(vinyl alcohol) (PVA), poly(vinylpyrrolidone) (PVP) and copolymers of the aforementioned polymers.

Typically, said linker to be used in the method of the disclosure is a low molecular weight (MW) polymer having a MW of between 0.01 to 5, between 0.01 to 1.0, between 0.01 to 0.5 or between 0.1 to 0.5 kDa, said polymer is poly(ethylene glycol) (PEG), poly(ethylene oxide), poly (propylene glycol), polyglycerol, polyacrylamide (PAM), polyethylineimine (PEI), polymethacrylate or another acrylic polymer, poly(vinyl alcohol) (PVA), poly(vinylpyrrolidone) (PVP) or a copolymer of the aforementioned polymers.

The application of the linker and the polymer are carried out under conditions allowing the formation of a spatial arrangement of the linker and the polymer which reflects the envisaged arrangement of detection molecules and polymer. This can be achieved by applying a predefined mixture of said molecules to the electrode surface. Typically, the linker and polymer molecules are mixed in an application solution in a predefined molar ratio. The molar ratio of the polymer and the linker for the detection agent is, typically, between 1:100 to 100:1, 1:50 to 50:1, 1:20 to 20:1, 1:10 to 10:1, 1:5 to 5:1, 2:10 to 8:1, 3:10 to 7:1, 4:10 to 6:1 or 5:10 to 5:1 in a suitable solvent. Said solvent is brought into contact with the electrode surface and conditions are applied allowing for the immobilization of the linker and the polymer on the said surface. Moreover, the linker and polymer are, usually, applied such that they are present in equal amounts per surface area throughout the electrode surface.

In particular, the linker for the detection agent is a low molecular weight polymer as recited above, more typically, being of the same class of polymers as the polymer capable of mediating the salting-out effect, i.e., both are a poly (ethylene glycol) (PEG), a poly(ethylene oxide), a poly (propylene glycol), a polyglycerol, a polyacrylamide (PAM), a polyethylineimine (PEI), a polymethacrylate or another acrylic polymer, a poly(vinyl alcohol) (PVA), a poly(vinylpyrrolidone) (PVP) or a copolymer of the aforementioned polymers. In the method of the disclosure, a suitable layer arrangement of polymer and detection agent can be, typically, obtained by applying the polymer and the aforementioned polymer linker as a solution in a suitable solvent to the electrode comprising the polymer and the linker in a molecular weight ratio of 1:10 to 1:50, more typically, 1:20. It is advantageous to use molecules of the same polymer classes as linker and polymer capable of mediating the salting-out effect since the same immobilization reaction can be used to immobilize said polymer and polymer linker to the surface of the electrode.

In the next step, the detection molecules are applied under conditions which allow for covalent or non-covalent attachment of the said at least one detection molecule to the electrode via the immobilized linker. The linker, typically, comprises a further functional group being capable of forming a covalent or non-covalent bound with the detection molecule. Typical functional groups include those specified elsewhere herein. Upon applying the detection agent to the electrode comprising linker and polymer molecules on its surface, the envisaged spatial arrangement is generated. In particular, the said at least one polymer capable of mediating a salting-out effect and the said at least one detection agent are present in equal amounts per surface area throughout the electrode surface. Moreover, the polymer capable of mediating a salting-out effect is arranged around the detection agent present in an amount allowing the reduction of the ionic strength of a fluid in proximity to the detection agent and allowing for binding an analyte comprised in a fluid sample.

The present disclosure also provides for an analyte detector for determining at least one analyte comprising the electrode of the present disclosure or an electrode obtainable by the method of the present disclosure, wherein said electrode is in electrical contact with a transducer or is part of the transducer.

The term "analyte detector" as used herein refers to a device which is suitable for the detection of at least one analyte in a fluid sample. The analyte detector shall comprise the electrode of the disclosure as analyzing component. Moreover, the said device shall comprise, typically, a loading element for introducing the fluid sample into the device and a contacting element which allows for contacting the electrode to the fluid sample. Further, the electrode shall be in electrical contact with a transducer or be a part of such a transducer. Typically, the analyte device according to the disclosure comprises a field-effect transistor (FET) and the electrode of the disclosure is used in the said transistor as a gate electrode or as a channel. When used as a gate electrode or as a channel, the electrode of the disclosure allows for a specific and efficient detection of an analyte in a fluid sample applying, e.g., the analyte detector according to the disclosure.

Alternatively, or additionally, the analyte device according to the disclosure may comprise an electrochemical measurement device and the electrode of the disclosure may take part in the electrochemical measurement. The term "electrochemical measurement device" may generally refer to an arbitrary device configured for performing at least one electrochemical measurement. For this purpose, the at least one electrochemical measurement device may comprise one or more electrical devices configured for performing the at least one electrochemical measurement. As an example, the electrochemical measurement device may comprise at least one electrode, at least one electrical source, such as at least one electrical source selected from the group consisting of: a constant voltage source, a variable voltage source, a constant electrical current source, a variable electrical current source, a frequency generator for generating periodic electrical signals. Further, the electrochemical measurement device may comprise at least one electrical measurement device configured for measuring at least one electrical signal or electrical measurement variable, such as at least one electrical measurement device selected from the group consisting of: a voltage measurement device, a current measurement device, a potentiostat. Other measurement devices are also feasible.

As used herein, the term "electrochemical measurement" may generally refer to the measurement of at least one measurable characteristic of a redox reaction. The electrochemical measurement and/or the measurable characteristic of the redox reaction, as an example, may imply an electrical current, a voltage, an electrical potential, a mass, for instance a mass deposited on an electrode, an impedance, particularly the real part and/or the imaginary part of the impedance.

Specifically, the electrochemical measurement may be performed in the presence of an electroactive species. As used herein, the term "electroactive species" may generally refer to a compound that facilitates or enhances or catalyzes the redox reaction, for instance by facilitating an electron transfer. The electroactive species may be dissolved in the fluid sample and/or may be immobilized on a surface of the analyte detector, wherein the surface may be exposable to the fluid sample. In particular, the surface may be the above-mentioned sensing surface and/or the above-mentioned surface of the multipurpose electrode. Typical examples of electroactive species are redox mediators, specifically redox couples, such as but not limited to: potassium ferricyanid/potassium ferrocyanide; hexaammineruthenium (II) chloride/hexaammineruthenium (III) chloride; ferrocene methanol. Further typical examples of electroactive species are reducing agents such as but not limited to ascorbic acid, glutathione, lipoic acid, uric acid, oxalic acid, tannins and phytic acid. The electroactive species may facilitate or enhance the measurement of the at least one measurable characteristic of the redox reaction.

Additionally, or alternatively, the electrochemical measurement may refer to a direct or indirect detection of an electrical property of an element, for example of the electrode, wherein the electrical property is influenced or affected by a chemical reaction and/or by a transfer of electrons and/or by a binding of an atom or a molecule. Specifically, the electrical property may be influenced or affected by a chemical reaction that comprises a change of an oxidation state of at least one of its participants. The electrical property may for example be an electrochemical potential and/or a change of the electrochemical potential of the element, an electrical potential and/or a change of the electrical potential of the element, a voltage and/or a change of the voltage applied to the element and/or the amount of charge accumulated on the element. The direct or indirect measurement of the electrical property of the element may be based on an electrical field effect caused by and/or influenced by the electrical property of the element. Thus, as a specific example, the chemical reaction may change the oxidation state of an element. The change of the oxidation state of the element may be measurable in the electrochemical measurement via an electrical field effect, which the oxidation state of the element may contribute to. Thus, the detection of the change of the oxidation state of an element may for example be detectable using a field effect transistor. In particular, the electrical property of the element may influence a current between a source electrode and a drain electrode of the field effect transistor by influencing a gate voltage of the field effect transistor.

The term "transducer" as used herein refers to any kind of functional component or an arrangement of functional components configured to convert energy from one form to another and/or configured to convert an input signal, in particular an electrical signal such as an electrical current, a voltage or a potential applied, into a corresponding output signal, wherein the form of the output signal is different from the form of the input signal. Thus, a transducer may be configured to produce an electrical signal of one form, e.g., an electrical current, as the output signal after having received another electrical signal, e.g., a voltage or a potential applied, as the input signal. Specifically, the transducer may be or may comprise the field-effect transistor and/or the electrochemical measurement device. In the case that the transducer is implemented as a field-effect transistor, the input signal may be the voltage or the potential applied to a channel of the field-effect transistor by the gate electrode, which can be modified by the binding of charged species on the sensor surface, while the output signal may be a drain current $I_d$ between a source electrode and a drain electrode of the field-effect transistor. In the case that the transducer is implemented as the electrochemical measurement device, the input signal may be the at least one measurable characteristic of the redox reaction.

The present disclosure contemplates, in general, the use of the analyte detector of the present disclosure for determining at least one analyte in a fluid sample. Typically, said determination of the at least one analyte in a fluid is involved in diagnostic purposes, environmental monitoring and control, food safety, quality control or manufacturing processes.

Detection of analytes plays a role, typically, in the various different processes. It may be used for diagnosis of analyte changes in a subject which in turn may aid diagnosis of diseases or other medical conditions. Further, the analysis of analytes may be useful in monitoring the environment, e.g., for detecting a change in the degree of pollution. Yet, production, food safety and general quality control processes typically require the detection of analytes. Thus, the analyte detector according to the disclosure may be used in any of such processes and, typically, allows for further automation thereof.

Moreover, the present disclosure contemplates a method for determining at least one analyte comprising the steps of: (a) contacting a fluid sample suspected to comprise the at least one analyte to the electrode of the disclosure or the analyte detector of the disclosure; and (b) performing an electrochemical measurement with said electrode or detector, whereby the at least one analyte will be determined.

The term "determining" as used in this context refers to quantitative determinations, i.e., determinations of the amount, as well as qualitative determinations, i.e., determinations of the presence or absence of an analyte. Such determinations may be carried out using, e.g., an analyte detector of the disclosure, by performing an electrochemical measurement as described elsewhere herein. Based on the results of the electrochemical measurement, the at least one analyte can be determined as mentioned above.

The electrochemical measurement can be performed, in principle, under standard conditions allowing for the binding of the analyte to the detection agent on the electrode. Such standard conditions may, typically, include a temperature being above the freezing point and below the boiling point of the fluid sample. In some applications, the temperature will be a temperature being within the range of room temperature. More typically, however, the electrochemical measurement is performed at a temperature between 30° C. and 40° C., typically, a temperature of at least 30° C., at least 32° C., at least 35° C. or at least 37° C. It has been found in the studies underlying the disclosure that a strong signal enhancement can be achieved if the measurements are performed at about 37° C., leading to 3 orders of magnitude lower detection limit compared to 21° C.

Performing an electrochemical measurement in the presence of an electroactive species may be, for example, carried out for signal enhancement. The electroactive species can be dissolved in the analyte solution or immobilized on the surface. Typical electroactive species are: redox couples such as potassium ferri/ferrocyanide, hexaammineruthenium (II) and (III) chloride, ferrocene methanol; reducing agents such as ascorbic acid, glutathione, lipoic acid, uric acid, oxalic acid, tannins, phytic acid. Performing an electrochemical or transistor-based measurement can be, typically, carried out in the presence of a secondary receptor attached to the surface-bound analyte for signal enhancement. The secondary receptor may enhance the signal and/or selectivity on its own or may be labelled with an additional molecule such as an enzyme. The signal enhancing molecule may produce, for example, through interaction with a substrate, a change in concentration of species directly measurable by the sensor such as protons or electrons.

The disclosure further provides and proposes a computer program including computer-executable instructions for performing the aforementioned method according to the present disclosure in one or more of the embodiments enclosed herein when the program is executed on a computer or computer network. Specifically, the computer program may be stored on a computer-readable data carrier. Thus, specifically, one, more than one or even all of method steps c) and d) as indicated above may be performed and/or controlled and/or evaluated by using a computer or a computer network, typically by using a computer program.

The disclosure further provides and proposes a computer program product having program code means, in order to perform the aforementioned method according to the present disclosure in one or more of the embodiments enclosed herein when the program is executed on a computer or computer network. Specifically, the program code means may be stored on a computer-readable data carrier.

Further, the disclosure provides and proposes a data carrier having a data structure stored thereon, which, after loading into a computer or computer network, such as into a working memory or main memory of the computer or computer network, may execute the aforementioned method according to one or more of the embodiments disclosed herein.

The disclosure further provides and proposes a computer program product with program code means stored on a machine-readable carrier, in order to perform the aforementioned method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the disclosure provides and proposes a modulated data signal that contains instructions readable by a computer system or computer network, for performing the aforementioned method according to one or more of the embodiments disclosed herein.

Typically, referring to the computer-implemented aspects of the disclosure, one or more of the method steps or even all of the method steps of the aforementioned method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present disclosure further provides:
- A computer or computer network comprising at least one processor, wherein the processor is adapted to perform the method according to one of the embodiments described above,
- a computer loadable data structure that is adapted to perform the method according to one of the embodiments described above while the data structure is being executed on a computer,
- a computer program, wherein the computer program is adapted to perform the aforementioned method according to one of the embodiments described in this description above while the program is being executed on a computer,
- a computer program comprising program means for performing the aforementioned method according to one of the embodiments described in this description above while the computer program is being executed on a computer or on a computer network,
- a computer program comprising program means according to the preceding embodiment, wherein the program means are stored on a storage medium readable to a computer,
- a storage medium, wherein a data structure is stored on the storage medium and wherein the data structure is adapted to perform the aforementioned method according to one of the embodiments described above after having been loaded into a main and/or working storage of a computer or of a computer network, and
- a computer program product having program code means, wherein the program code means can be stored or are stored on a storage medium, for performing the aforementioned method according to one of the embodiments described above, if the program code means are executed on a computer or on a computer network.

The following typical embodiments shall illustrate the disclosure further but shall not be construed, whatsoever, as limitations:

Embodiment 1

An electrode comprising a functionalized surface exposable to a fluid sample, said functionalized surface comprises at least one polymer capable of mediating a salting-out effect and at least one detection agent that binds to an analyte comprised in the fluid sample, wherein the said at least one polymer capable of mediating a salting-out effect and the said at least one detection agent are distributed on the surface of the electrode such that the detection agent is present in essentially equal amounts per surface area throughout the electrode surface and the polymer capable of mediating a salting-out effect is arranged around the detection agent present in an amount i) allowing the reduction of the ionic strength of the fluid in proximity to the detection agent, and ii) allowing for binding an analyte comprised in the fluid sample.

Embodiment 2

The electrode of embodiment 1, wherein said electrode comprises graphene, carbon nanotubes, carbon, silicon nanowires, molybdenum oxide, molybdenum disulfide, titanium oxide, zinc oxide, a metal oxide, gallium nitride, gold, silver, platinum, silicon, magnetic beads, nanoparticles or any combination of these materials.

Embodiment 3

The electrode of embodiment 1 or 2, wherein the size of the said at least one polymer capable of mediating a salting-out effect is such that the Debye length is increased and the ionic strength around the at least one detection molecule is reduced.

Embodiment 4

The electrode of embodiment 3, wherein the molecular weight (MW) of the said at least one polymer capable of mediating a salting-out effect is between 1 and 100 kDa, between 10 and 100 kDa, between 10 and 50 kDa, between 10 and 25 kDa, between 10 and 20 kDa or between 10 and 15 kDa.

Embodiment 5

The electrode of any one of embodiments 1 to 4, wherein said at least one polymer capable of mediating a salting-out effect is selected from the group consisting of: poly(ethylene glycol) (PEG), poly(ethylene oxide), poly(propylene glycol), polyglycerol, polyacrylamide (PAM), polyethylineimine (PEI), polymethacrylate or another acrylic polymer, poly(vinyl alcohol) (PVA), poly(vinylpyrrolidone) (PVP), copolymers of the aforementioned polymers, polysaccharides, polypeptides, polynucleotides and polysiloxanes.

Embodiment 6

The electrode of any one of embodiments 1 to 5, wherein said at least one polymer capable of mediating a salting-out effect is immobilized on the surface of the electrode via a linker or directly attached via a functional group without an additional linker.

Embodiment 7

The electrode of embodiment 6, wherein said linker is a linker having the following structure:

A-B—C wherein A is a first functional group from the classes: thiol, silane, phosphonic acid, aromatic molecules (e.g., pyrene), carboxyl, amine, NHS ester, maleimide, wherein B is a short organic chain from the following classes: low molecular weight polymer from the classes described above, hydrocarbons (e.g., alkyl, alkenyl, alkynyl, phenyl), oxygen containing groups (e.g., ether), haloalkanes (e.g., chloro), nitrogen containing groups (e.g., amide), sulfur containing groups (e.g., sulfoxide), phosphorus containing groups, boron containing groups, or a short inorganic polymer chain (e.g., Si-based (siloxane), P-based, B-based, S-based), and wherein C is a second functional group from the classes: carboxyl, amine, NHS ester, maleimide.

Embodiment 8

The electrode of any one of embodiments 1 to 7, wherein said at least one detection agent specifically binds to the analyte comprised in the fluid sample.

Embodiment 9

The electrode of embodiment 8, wherein said at least one detection agent is selected from the group consisting of: antibodies and fragments thereof, nucleic acids, aptamers, peptide nucleic acids (PNAs), receptor or ligand proteins or peptides, and enzymes.

Embodiment 10

The electrode of any one of embodiments 1 to 9, wherein the size of the at least one detection agent is such that the detection agent is surrounded by the at least one polymer capable of mediating a salting-out effect.

Embodiment 11

The electrode of any one of embodiments 1 to 10, wherein said at least one detection agent is immobilized on the surface of the electrode via a linker.

Embodiment 12

The electrode of embodiment 11, wherein said linker is a linker as defined in embodiment 7.

Embodiment 13

The electrode of embodiment 11, wherein said linker is selected from the group consisting of: a low molecular weight (MW) polymer having a MW of between 0.01 to 5, between 0.01 to 1.0, between 0.01 to 0.5 or between 0.1 to 0.5 kDa, said polymer is poly(ethylene glycol) (PEG), poly(ethylene oxide), poly(propylene glycol), polyglycerol, polyacrylamide (PAM), polyethylineimine (PEI), polymethacrylate or another acrylic polymer, poly(vinyl alcohol) (PVA), poly(vinylpyrrolidone) (PVP) and a copolymer of the aforementioned polymers.

Embodiment 14

The electrode of embodiment 13, wherein the polymer capable of mediating a salting-out effect is of the same class of polymers as the linker polymer.

Embodiment 15

The electrode of any one of embodiments 1 to 14, wherein the molar ratio of the at least one polymer capable of mediating a salting-out effect and the at least one detection agent present on the functionalized surface is between 1:100 to 100:1, 1:50 to 50:1, 1:20 to 20:1, 1:10 to 10:1, 1:5 to 5:1, 2:10 to 8:1, 3:10 to 7:1, 4:10 to 6:1 or 5:10 to 5:1.

Embodiment 16

A method for manufacturing a functionalized surface on an electrode comprising the steps of:
a) applying to the electrode a linker and at least one polymer capable of mediating a salting-out effect under conditions which allow for covalent or non-covalent immobilization of the said linker and the said polymer on the surface of the electrode; and
b) applying at least one detection agent to the electrode upon immobilization of the said linker and the said polymer under conditions which allow for covalent or non-covalent attachment of the said at least one detection molecule to the electrode via the immobilized linker; and
wherein the conditions allow for distributing the said at least one polymer capable of mediating a salting-out effect and the said at least one detection agent on the surface of the electrode such that the detection agent is present in equal amounts per surface area throughout the electrode surface and the polymer capable of mediating a salting-out effect is arranged around the detection agent present in an amount
i) allowing the reduction of the ionic strength of a fluid in proximity to the detection agent, and
ii) allowing for binding an analyte comprised in a fluid sample.

Embodiment 17

The method of embodiment 16, wherein said linker is a low molecular weight (MW) polymer having a MW of between 0.01 to 5, between 0.01 to 1.0, between 0.01 to 0.5 or between 0.1 to 0.5 kDa, said polymer is poly(ethylene glycol) (PEG), poly(ethylene oxide), poly(propylene glycol), polyglycerol, polyacrylamide (PAM), polyethylineimine (PEI), polymethacrylate or another acrylic polymer, poly(vinyl alcohol) (PVA), poly(vinylpyrrolidone) (PVP) or a copolymer of the aforementioned polymers.

Embodiment 18

The method of embodiment 16 or 17, wherein said at least one polymer capable of mediating a salting-out effect is selected from the group consisting of: poly(ethylene glycol) (PEG), poly(ethylene oxide), poly(propylene glycol), polyglycerol, polyacrylamide (PAM), polyethylineimine (PEI), polymethacrylate or another acrylic polymer, poly (vinyl alcohol) (PVA), poly(vinylpyrrolidone) (PVP) and copolymers of the aforementioned polymers.

Embodiment 19

The method of embodiment 17 or 18, wherein the polymer capable of mediating a salting-out effect is of the same class of polymers as the linker polymer.

Embodiment 20

The method of any one of embodiments 16 to 19, wherein the molar ratio of the at least one polymer capable of mediating a salting-out effect and the at least one detection agent present on the functionalized surface is between 1:100 to 100:1, 1:50 to 50:1, 1:20 to 20:1, 1:10 to 10:1, 1:5 to 5:1, 2:10 to 8:1, 3:10 to 7:1, 4:10 to 6:1 or 5:10 to 5:1.

Embodiment 21

An analyte detector for determining at least one analyte comprising the electrode of any one of embodiments 1 to 15 or an electrode obtainable by the method of any one of embodiments 16 to 20, wherein said electrode is in electrical contact with a transducer or is part of the transducer.

Embodiment 22

Use of the analyte detector of embodiment 21 for determining at least one analyte in a fluid sample.

Embodiment 23

A method for determining at least one analyte comprising the steps of:
(a) contacting a fluid sample suspected to comprise the at least one analyte to the electrode of any one of embodiments 1 to 15 or the analyte detector of embodiment 21; and
(b) performing an electrochemical measurement with said electrode or detector, whereby the at least one analyte will be determined.

Embodiment 24

The method of embodiment 23, wherein said electrochemical measurement is performed at a temperature between 30° C. and 40° C., typically, a temperature of at least 30° C., at least 32° C., at least 35° C. or at least 37° C.

Embodiment 25

The use of embodiment 22 or the method of embodiment 23 or 24, wherein said determination of the at least one analyte in a fluid is involved in diagnostic purposes, environmental monitoring and control, food safety, quality control or manufacturing processes.

Embodiment 26

The electrode of any one of embodiments 1 to 15, the method of any one of embodiments 16 to 20 or the use of embodiment 22 or the method of embodiments 23 or 24 or the use or method of embodiment 25, wherein said fluid sample is a liquid or dissolved environmental sample or a solution of at least one chemical compound.

Embodiment 27

The electrode of any one of embodiments 1 to 15, the method of any one of embodiments 16 to 20 or the use of embodiment 22 or the method of embodiments 23 or 24 or the use or method of embodiment 25 or 26, wherein said fluid is a high ionic strength fluid.

Embodiment 28

The electrode, method or use of embodiment 27, wherein said fluid is a body fluid.

Embodiment 29

The electrode, method or use of embodiment 28, wherein said body fluid is selected from the group consisting of: blood, plasma, serum or any fraction thereof, saliva, tears, mucus, lymph, cerebrospinal fluid, urine, feces, sweat, semen, synovial fluid.

All references cited in this specification are herewith incorporated by reference with respect to their entire disclosure content and the disclosure content specifically mentioned in this specification.

EXAMPLES

The disclosure will be described by way of Examples. However, the Examples shall merely illustrate the disclosure and not be construed, whatsoever, as limiting the scope of the disclosure.

Example 1: Polyethylene Glycol Reduces the Effect of Debye Screening in Transistor-Based DNA Detection QCM-D measurements: They were performed with a Q-sense E4 from Biolin Scientific AB (Stockholm, Sweden) using their electrochemistry module. The QCM-D simultaneously monitors the shifts in oscillator frequency (Of) and energy dissipation (ΔD) on a 4.95 MHz, gold-coated, QCM-D sensor, at different overtones. Furthermore, the Q-sense's electrochemistry module allows for the simultaneous FET measurements. Prior to use, gold-coated sensors were cleaned with UV/ozone treatment for 10 min then immersed in a solution containing 1 part $H_2O_2$ (30%)+1 part $NH_4OH$+5 parts deionized (DI) water at 80° C. for 10 min. The sensors were then extensively washed with DI water and dried with $N_2$ gas. All experiments were performed using freshly cleaned sensors.

Extended-Gate FET measurements: The electrochemistry module used in the QCMD experiments allowed to electrically connect the gold-coated sensor to the gate terminal of a commercial MOSFET. An Ag/AgCl reference electrode (WPI, Dri-REF™, customized length) is placed near the sensor surface in the outlet flow channel. Electrical measurements were performed using a dual-channel sourcemeter (Keithley 2636B).

dsDNA preparation and immobilization: Complementary single-strand DNA (i): 5'-CAATGCAGATACACTTTTTT-C3H6-SH-3' (SEQ ID NO:1) (ii): 5'-AGTGTATCTG-CATTG-3' (SEQ ID NO:2) were purchased from STAB vida, Portugal. Strand (i) is thiolated to facilitate immobilization on gold surface. Thiolated methoxy polyethylene glycol (mPEG-SH) with average molecular weight of 10 kDa was purchased from Nanocs, Inc. (Boston, MA). All other reagents, unless stated otherwise, were purchased from Sigma-Aldrich.

Formation of (A) dsDNA, (B) PEG, and (C) mixed dsDNA-PEG layer: The formation of all 3 different surfaces was monitored by both QCM-D and FET measurements. Thiolated double-stranded DNA (dsDNA) was formed by mixing equimolar solutions of strands (i) and (ii) (10 μL each of 100 μM stock solution stored at −20° C.) for 30 min in 100 mM PBS, at room temperature, prior to every experiment. And thiolated mPEG solution (5 mM) was prepared by dissolving the PEG powder in water, prior to every experiment. (A) dsDNA SAM: A monolayer of dsDNA was formed on the gold-coated QCM-D sensor by injecting 1 μM thiolated dsDNA in Buffer A (1 M NaCl, 1 mM EDTA in 10 mM Tris pH 7) at 100 μL/min for 10 min, then allowed to incubate for 1 hr. The surface was then washed with Buffer A for 10 min at 100 μL/min. After washing-off the excess dsDNA, different concentrations of PBS solution (200 mM, 100 mM, 50 mM, 10 mM, and 1 mM) was injected into the chamber (100 μL/min for 10 min) and the FET response was recorded until a stable signal was achieved. (B) PEG SAM: Similar to A except that 1 µM thiolated mPEG (average MW=10 kDa) was injected to form the PEG monolayer. (C) mix dsDNA-PEG layer: A monolayer of dsDNA was formed first by incubating the sensor surface with 1 µM thiolated dsDNA. Afterwards, the excess dsDNA was washed off by flowing 100 µL/min of Buffer A for 10 min. The PEG was added into the monolayer of dsDNA by injecting 1 uM mPEG-SH in Buffer A into the chamber and incubating for 20 min before washing-off the unbound PEG molecules by flowing 100 uL/min Buffer A for 10 min. Similar to A and B, different concentrations of PBS solution was then injected into the chamber to monitor the FET response of the mixed layer under different ionic strength conditions.

Figure 1C:
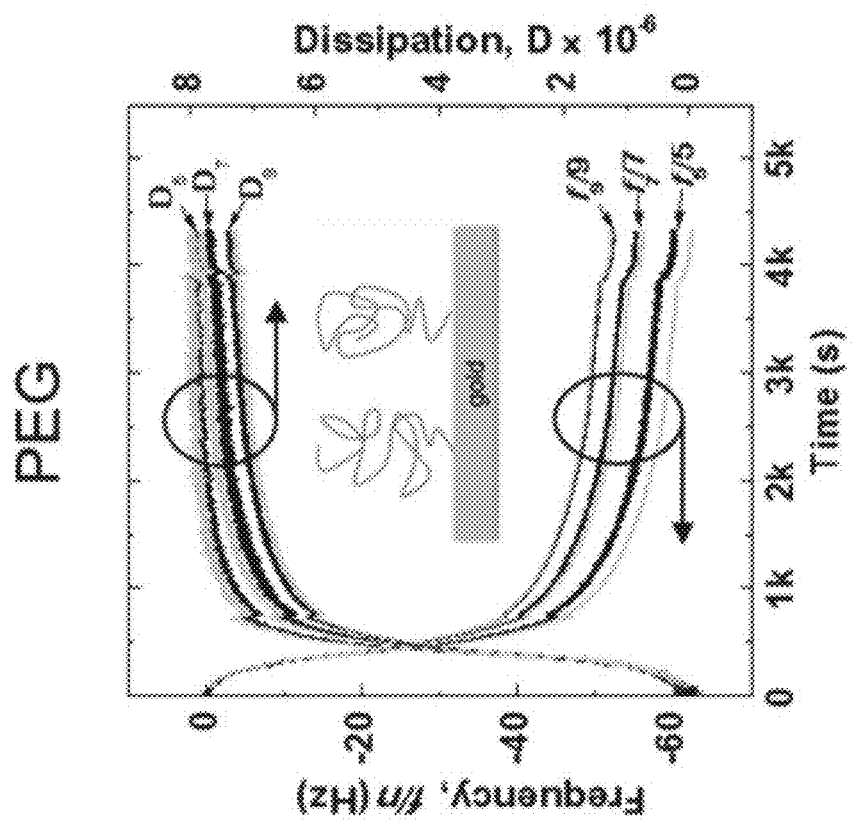
Figure 1F:
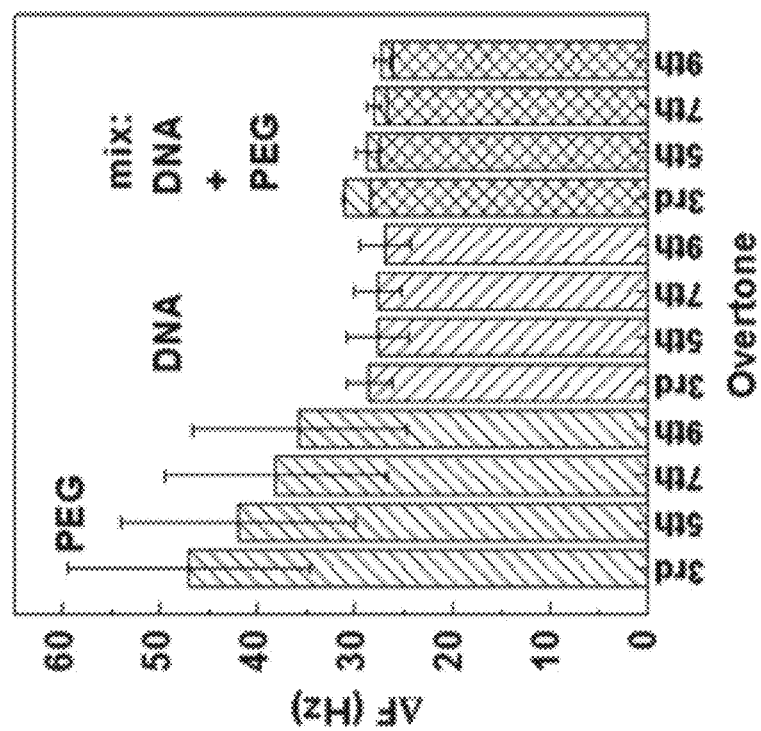
Figure 1E:
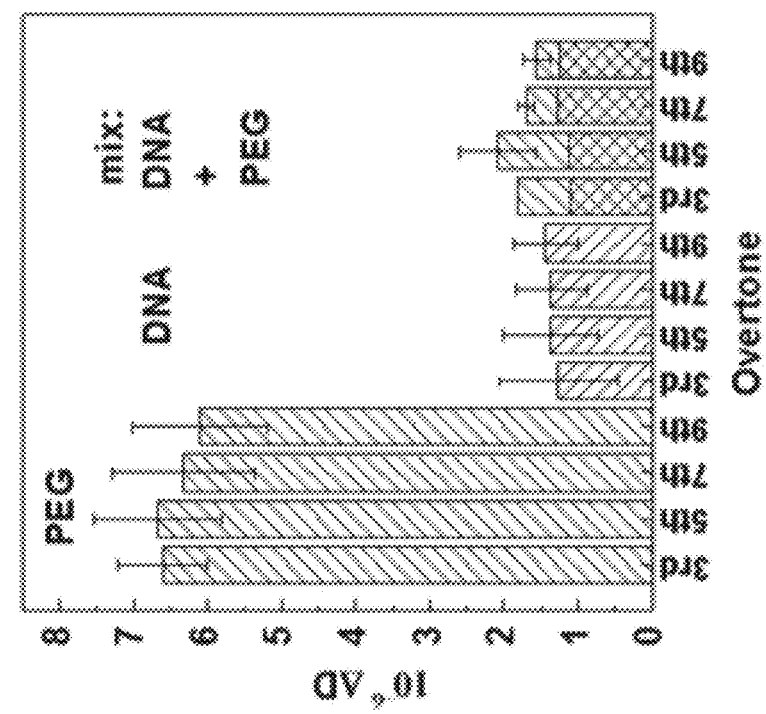

Surface Characterization: The formation of monolayers of dsDNA, PEG, and mix dsDNA+PEG layer on gold-coated quartz crystal was characterized using quartz crystal microbalance with dissipation (QCMD). In QCMD, changes in the resonance frequency and dissipation energy of the oscillating piezoelectric quartz crystal are measured in response to mass adsorption on the crystal's surface (FIG. 1A). These are then used to obtain viscoelastic properties, as well as the density, mass and thickness of the adsorbed layer. FIGS. 1B-1D show the changes in resonance frequency, Of, and the changes in the dissipation factor, ΔD, from different overtones (n=3 (not shown in FIGS. 1B-1D), 5, 7, 9) upon (b) dsDNA, (c) PEG, and (d) mix dsDNA+PEG layer immobilization on gold-coated quartz crystal. The average ΔD and Δf calculated from 3 separate trials for each layer are shown in the bar graphs FIGS. 1E and 1F, respectively. It is worth noting that even though the detected Δf for PEG (−Δf=35-45 Hz) is less than twice that of dsDNA (−Δf=about 25 Hz), the dissipation change is about 6× greater. This is consistent with the fact that dsDNA behave like a more rigid layer on the surface while PEG is known to form highly hydrated brush like structures when immobilized. This is also evident on the spreading of the Δf and ΔD upon PEG immobilization compared to dsDNA where all the overtones are changed with the same magnitude.

Voigt viscoelastic modelling is used to fit the QCMD data for all three different layers and obtain the parameters describing the physical properties of the layers formed. The fitted parameters are listed in Table 1.

TABLE 1

Parameters derived from Voigt viscoelastic modelling of QCMD results

|  | Thickness (nm) | Viscosity ($10^{-3}$ Pa-s) | Shear Modulus ($10^5$ Pa) | Wet Areal Mass (ng-cm$^{-2}$) |
|---|---|---|---|---|
| dsDNA | 5.1 +/− 0.7 | 4.7 +/− 0.7 | 13 +/− 6 | 510 +/− 38 |
| PEG | 9 +/− 2 | 1.8 +/− 0.3 | 2.6 +/− 0.5 | 1053 +/− 228 |
| Mix |  |  |  |  |
| dsDNA | 5.1 +/− 0.1 | 4.9 +/− 0.1 | 10.0 +/− 0.3 | 535 +/− 24 |
| PEG | 0.7 +/− 0.2 | 1.1 +/− 0.1 | 0.9 +/− 0.3 | 73 +/− 25 |

The measured thickness of dsDNA is about 5 nm in 1 M NaCl which is close to the expected length for 15 base-pair dsDNA (5 nm) plus linker (1 nm). This indicates that dsDNA molecules are vertically immobilized and not lying flat on the surface. The PEG (10 kDa) layer is thicker at about 9 nm when 1 µM PEG is used for immobilization. The viscoelastic modeling results also show that the shear viscosity and shear modulus of dsDNA (4.7+/−0.7 mPa·s and 1.3+/−0.6 MPa, respectively) are both higher than that of PEG (1.8+/−0.3 mPa·s and 0.26+/−0.05 MPa, respectively). These viscoelastic parameters suggest that dsDNA on gold form a more rigid layer compared to PEG. Our results are consistent with previous studies that show dsDNA form fairly rigid films while PEG are known to form soft, brush like structures on surfaces.

In the mixed layer, where the two components were added successively, modelling each step can be done independently. As shown in Table 1, since dsDNA was immobilized first, the fitting parameters are consistent with dsDNA-only layer. Based on these results, the surface is coverage is estimated to be 60%. Then, PEG was added, which is electrically neutral, and could potentially bind to the empty spaces in between dsDNA molecules. Changes in both dissipation and frequency upon addition of PEG proved that PEG was successfully added to the dsDNA layer producing a mixed film.

FET Measurements: The QCMD device that was used to characterize all three different surfaces comes with an electrochemistry module, which allows for FET measurements to be done simultaneously on the same chips, using the extended gate FET (EGFET) configuration. In this particular EGFET setup, the gold surface of the QCM chip is electrically connected to the gate terminal of a commercial MOSFET (FIG. 2A). The sensing surface with the biological solution is separated from the MOSFET readout transistor. This reduces the complexity of the sensing chip and protects the readout transistor from the contact to the solution, while retaining the charge sensitivity of a conventional ion-sensitive FET (Tarasov 2016, 2D Mater. 2: 044008; Tarasov 2016, Biosens. Bioelectron. 79: 669). To study the effect of PEG on the Debye screening of dsDNA via EGFET measurements, the transfer curves obtained from gold-immobilized dsDNA were compared to the mix dsDNA+PEG layer, under different ionic strength solutions (1-200 mM PBS) (FIG. 2). As a negative control, the response of gold-only surface was also measured upon changing the ionic strength (FIG. 2B). The transfer curve of the MOSFET shifts to more positive values with increasing PBS concentration (FIGS. 2B and 2D). This positive potential shift implies detection of negative ions adsorbing on gold surface, as previously observed in the case of Cl$^-$ ions and gold (Tarasov 2012, ACS Nano 6: 9291).

Figure 2E:
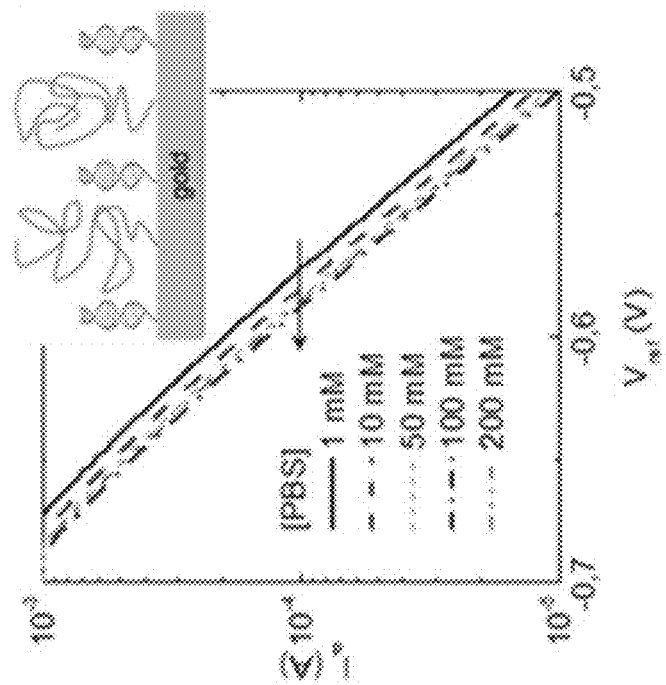
Figure 2D:
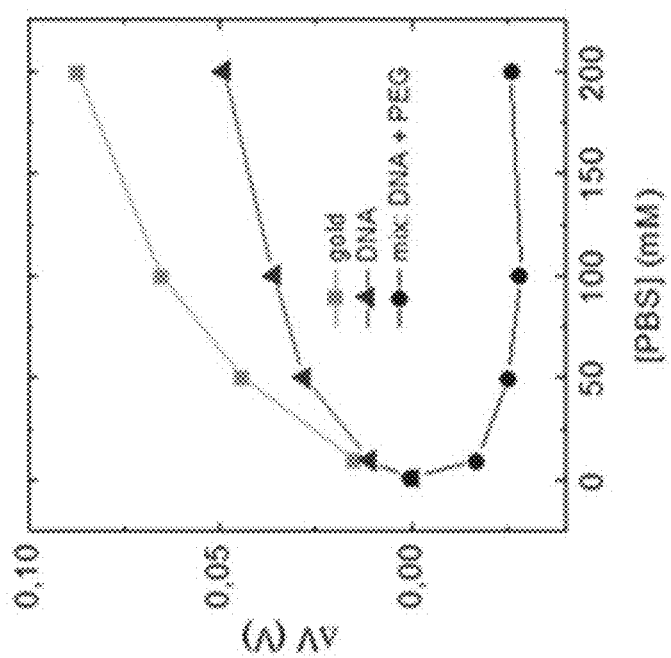

In the presence of dsDNA, the transfer curve still shifts to the right with increasing PBS concentration, but to a lesser degree compared to Au-only surface (FIG. 2C and FIG. 2D). In the absence of anion adsorption to gold, the expected effect of increasing ionic strength on dsDNA detection should shift the potential towards more negative values. However, due to this background anion adsorption, a positive potential shift is still observed with increasing ionic strength. The differential signal ($\Delta V = \Delta V_{dsDNA} - \Delta V_{Au-only}$) under different PBS concentrations was therefore obtained in order to see the effect of ionic screening on dsDNA measurements. In the mix layer, on the other hand, the presence of PEG made the detection of negative charges on dsDNA more pronounced. This time, increasing PBS concentration shifts the potential to the left (FIG. 2E and FIG. 2D). Upon background subtraction, the shift in signal is therefore higher in the presence of PEG than without.

These transistor-based measurements show that there is signal enhancement detected from dsDNA, even at 200 mM PBS, once PEG is present on the sensor surface. This indicates that PEG, at the concentration used in our experiments, does increase the Debye length even under physiological salt concentration. This could be due to the salting out effect that PEG exhibits in certain aqueous salt solutions and is characterized by the separation of a PEG-rich phase and a salt-rich phase over part of the composition space of a ternary water+PEG+salt system. It is believed that this tendency of PEG to "salt-out" ions is the reason behind the decrease in the effective ionic concentration in the areas immediately surrounding the PEG molecules. This "locally-desalted" region therefore will exhibit a relatively higher Debye length with respect to the apparent ionic strength.

Figure 3B:
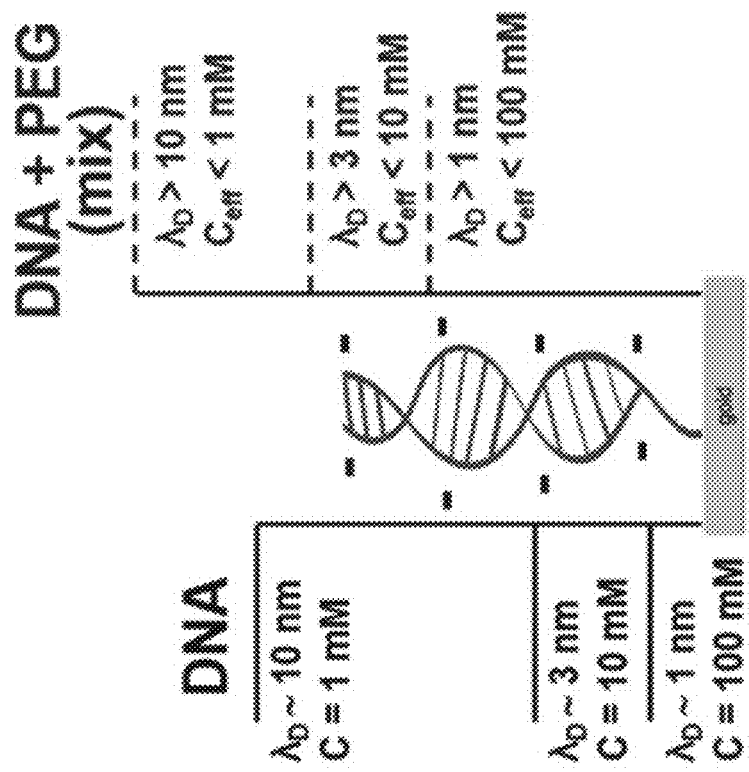
FIG. 3B shows the proposed model: addition of PEG increases the effective Debye length. As a result, a larger portion of DNA can be seen at a given ionic strength leading to a larger signal.
Figure 3A:
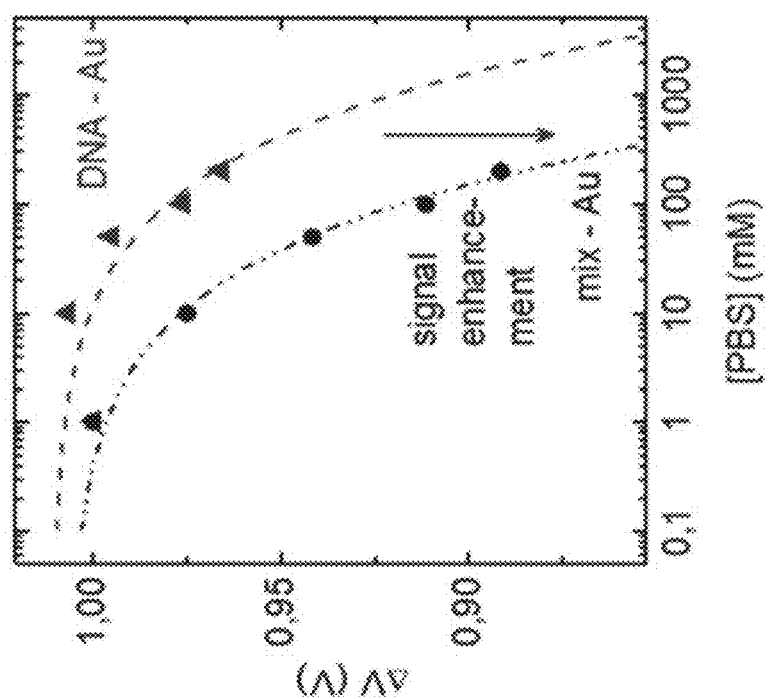
FIG. 3A shows FET data from FIG. 2 after subtracting the gold background. The potential shifts to more negative values with increasing PBS concentration, because the DNA screening by the electrolyte ions is stronger. Clear signal enhancement is observed for PEG+DNA mix vs. bare DNA.

FIG. 3A shows the signal enhancement achieved when PEG is mixed with dsDNA on the sensor surface. The downward and upward pointing triangles are the ionic strength dependence of dsDNA's FET signal in the absence and presence of PEG, respectively. This is the same data as shown in FIG. 2D, normalized by subtracting the background signal measured with bare gold. This data demonstrate that the signal is enhanced at least 3-4× when PEG is present (mix). With the salt dilution model schematically shown in FIG. 3B, we then compared the normalized data for dsDNA detection in the absence and presence of PEG. The upper dashed line in FIG. 3A shows the Debye length dependence with respect to the total ionic strength. Considering that PEG reduces the concentration of ions in the vicinity of dsDNA, we calculated the expected signal after a series of ionic strength dilutions. Upon reaching at least 10× dilution, the expected signal (FIG. 3A, lower dashed line) now overlaps with the signal obtained in the presence of PEG (FIG. 3A, upward triangles). This implies that with our experimental conditions we can achieve at least 10× dilution of ionic concentration in the mix layer with PEG, therefore enhancing the dsDNA signal by at least 3×.

It has been demonstrated that by addition of PEG to the sensor surface, the effect of ionic screening on the transistor-based detection of dsDNA can be mitigated. Measurements done on gold electrode using EGFET show that PEG enhances the signal from dsDNA by at least 3×, even under high ionic strength solutions (up to 200 mM PBS). This reduction of ionic screening can be attributed to the tendency of PEG to exclude ionic species in its immediate surrounding areas (salting-out effect). This implies that with enough PEG molecules present on the sensor surface, a locally-desalted region within the PEG layer is created. Thus, even in the presence of high ionic strength solutions, the region within the PEG layer on the sensor surface have effectively lower ionic strength environment compared to regions above the PEG layer. This increases the Debye length within the region next to the sensor surface therefore increasing the range of detection much further away from the surface.

The application of PEG can be extended to other type of biosensors as well. The crucial part is that the amount of PEG and receptors on the surface should be tuned in order to maximize receptor density and desalting effect at the same time. In addition to mitigating the ionic screening, PEG has also been shown to be effective in preventing non-specific interactions and in making the biomolecule more stable on the sensor surface. With all these advantages, the incorporation of PEG on the surface of transistor-based bio sensors can have tremendous impact in pushing FET biosensors towards PoC applications.

Example 2: Biodetection in High Ionic Strength Solutions Using PEGylated Carbon Nanotube Transistors with Nanobody Receptors FET-based biosensors are made from high quality, sorted semiconducting carbon nanotube networks that provide a sensitive and stable transducer with a scalable fabrication process. A combined surface functionalization scheme is proposed to overcome the Debye screening: 1) short nanobodies ($V_HH$) are used as receptors to enable analyte binding closer to the surface and 2) a polyethylene glycol (PEG) layer is added to increase the effective Debye length. Using green fluorescent protein (GFP) as a model system, a threefold signal enhancement is demonstrated with PEGylated surface in high ionic strength solutions. The mechanism is explained in terms of a local buffer dilution by PEG, mediated by the salting-out effect. The sensor reaches sub-pM detection limit with a dynamic range exceeding 4 orders of magnitude. In addition, the sensor is highly specific with negligible contributions from non-specific adsorption, if additional surface passivation is performed.

Immobilization of nanobodies (mixed Self Assembled Monolayer (SAM) formation): After fabrication of CNT FETs as described previously, (Rother 2016, ACS Appl. Mater. Interf. 8: 5571) the CNTs were cleaned with ethanol for 1 h to remove leftover polymer/contaminants from the CNT sorting process. Subsequently, the CNT electrode was treated with 1 mM pyrene butyric acid (PBA, linker)+0.25 mM pyrene-PEG (10 kDa) in ethanol for 1 h. Afterwards, it was briefly flushed with ethanol, $H_2O$ and then kept overnight in 100 mM Tris pH 7.4. Then, after brief flush with distilled water, 100 mM N-hydroxysuccinimide (NHS) and 1-Ethyl-3-(3-dimethylaminopropyl) carbodiimide (EDC) aqueous solution was pumped into the channel for 20 minutes to activate the surface. After that, either a 10 μM GFP-specific VHH nanobody or 10 μM bovine serum albumin (BSA), in 0.2 M phosphate buffer (pH 7) was introduced for 1 h for specific and non-specific adsorption experiments respectively. The surface was then flushed with 100 mM Tris for 15 min to deactivate possible leftover active sites. Finally, in case of optimized CNT FET based GFP sensing assay, the surface was exposed to 100 nM BSA solution in 100 mM Tris for 30 min to reduce the non-specific binding.

GFP binding measurements: Electrode was flushed with specified concentration of green fluorescent protein (GFP) in 1 mM Tris pH 7.4 for 15 minutes and 3 consecutive measurements were carried out. Afterwards, the electrode was flushed with the same concentration of GFP in 100 mM Tris pH 7.4 for 15 minutes and, again, 3 consecutive measurements were carried out. These measurements and treatments were repeated for the whole concentration range from 0 to 100 nM GFP.

Figure 4A:
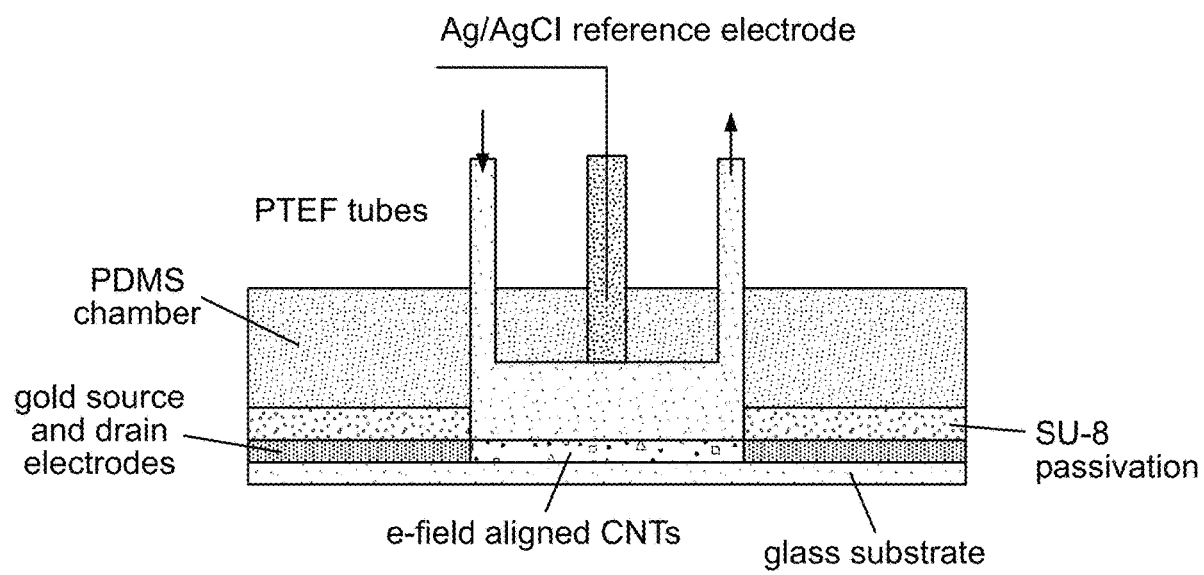
Figure 4B:
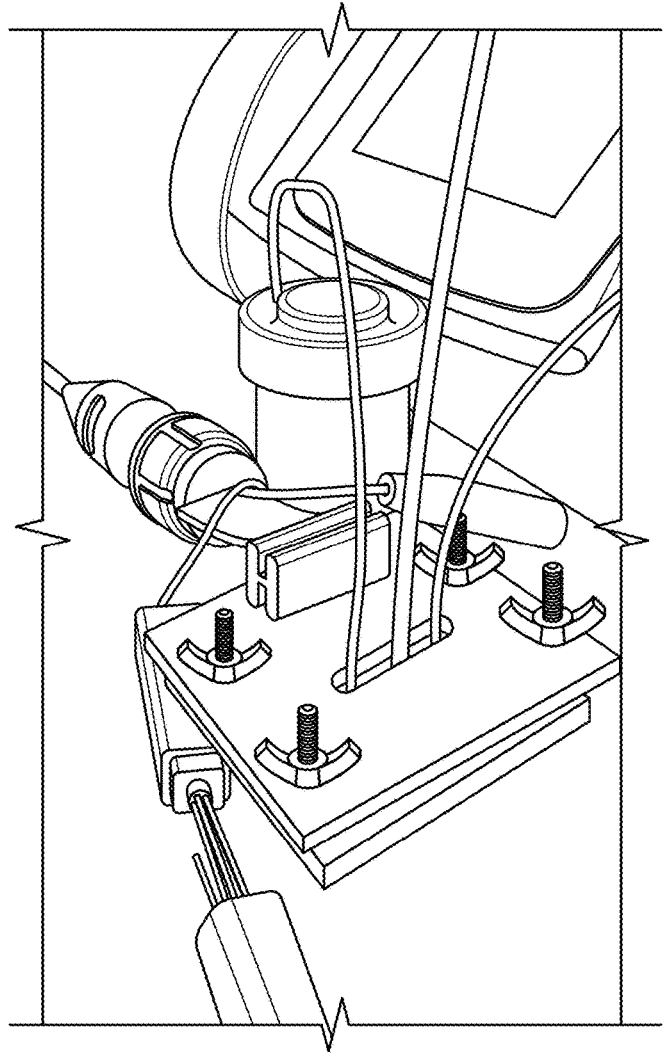

The CNT FETs were operated in a liquid-gated configuration, as shown in FIG. 4A. A photograph of the measurement setup is provided in FIG. 4B. The CNTs were polymer-sorted and aligned in an electric field following a previously published protocol (Rother 2016, ACS Appl. Mater. Interf. 8: 5571). Typical transistor transfer curves are presented in FIG. 4C. All devices exhibited ambipolar behavior with small hysteresis, current on-off ratios exceeding $10^4$, and steep subthreshold swings below 110 mV/dec. An AFM image of a typical device is shown in FIG. 4D.

Figure 5B:
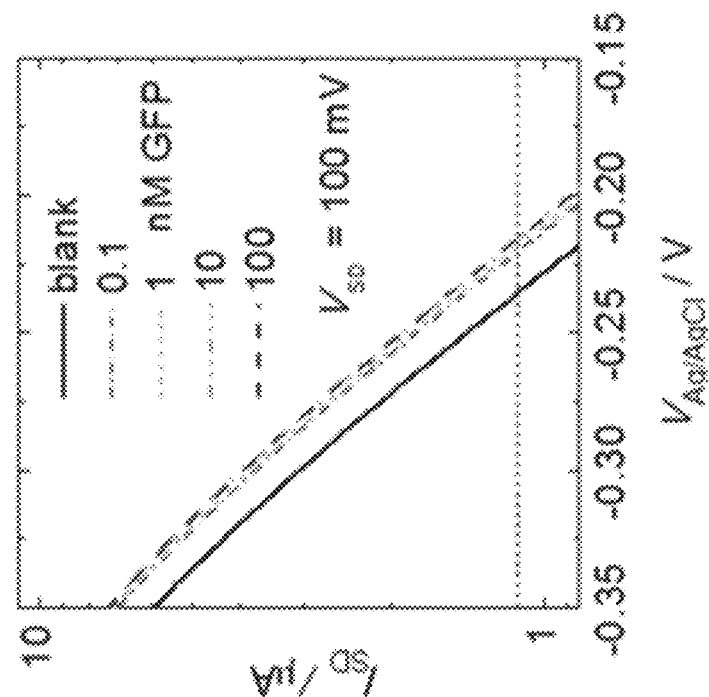
FIGS. 5A-5F show a comparison of GFP detection with PEGylated (FIGS. 5A-5C) and non-PEGylated CNT FETs (FIG. 5D-5F). The surface of the CNTs was modified either with a mixture of pyrene butyric acid (PBA) with pyrene poly(ethylene glycol) (FIG. 5A) or with PBA only (FIG. 5D). Camelid nanobodies (VHH), specific to green fluorescent protein (GFP), were then immobilized on both surfaces and exposed to GFP solutions to assess the VHH-GFP binding.
Figure 5A:
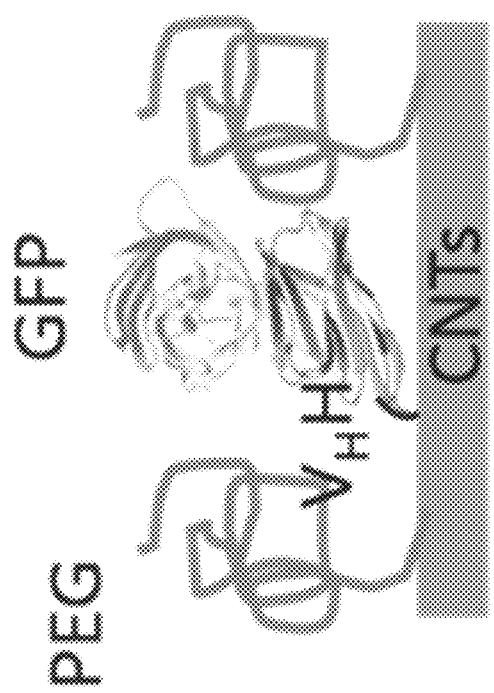
Figure 5D:
Figure 5C:
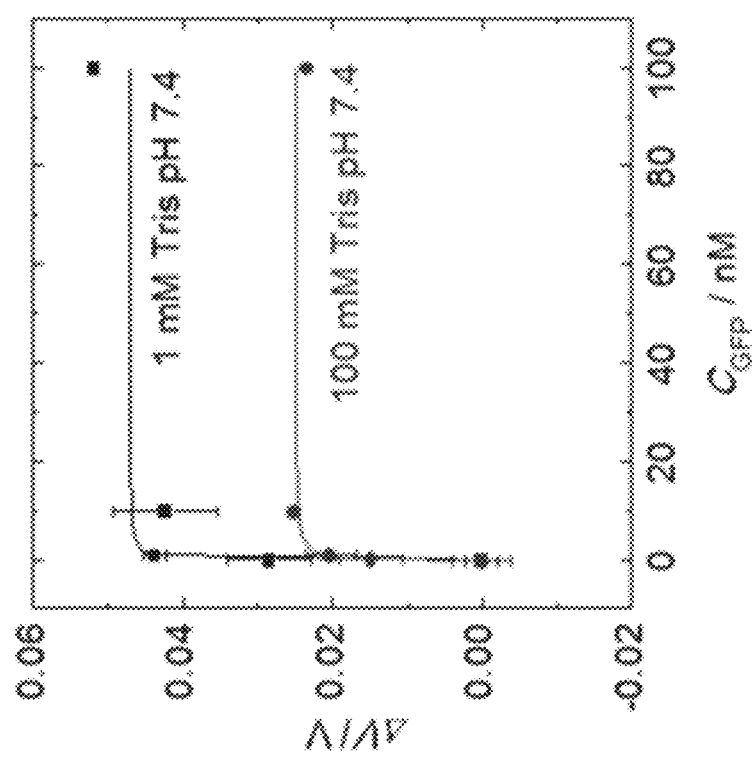
Figure 5F:
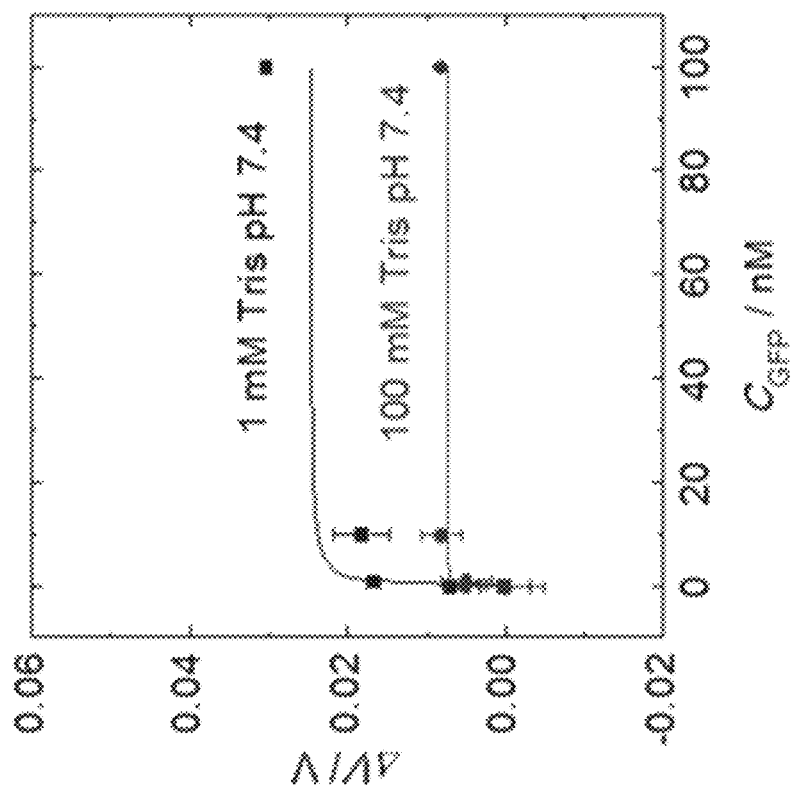
Figure 5E:
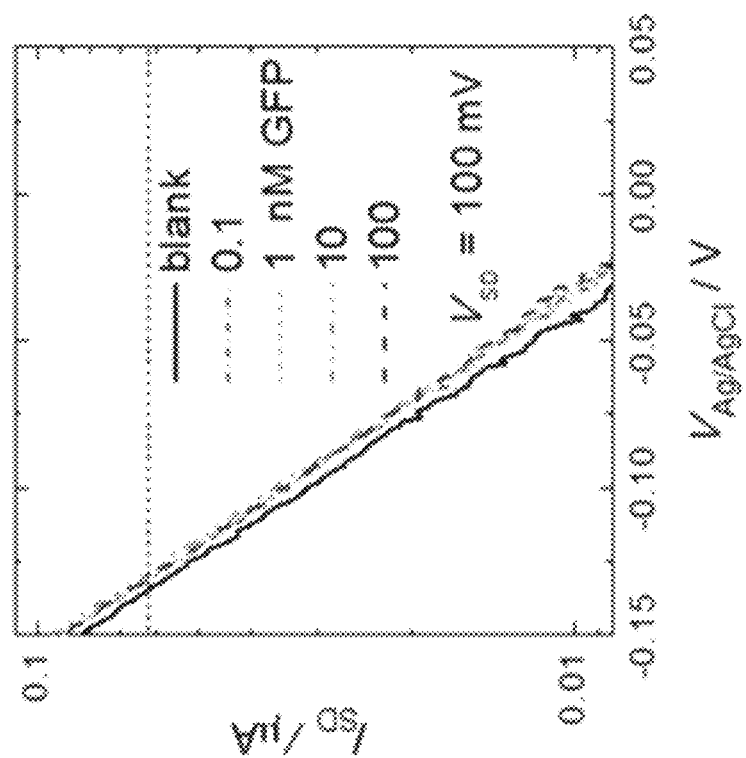
Figures 6A, 6B:
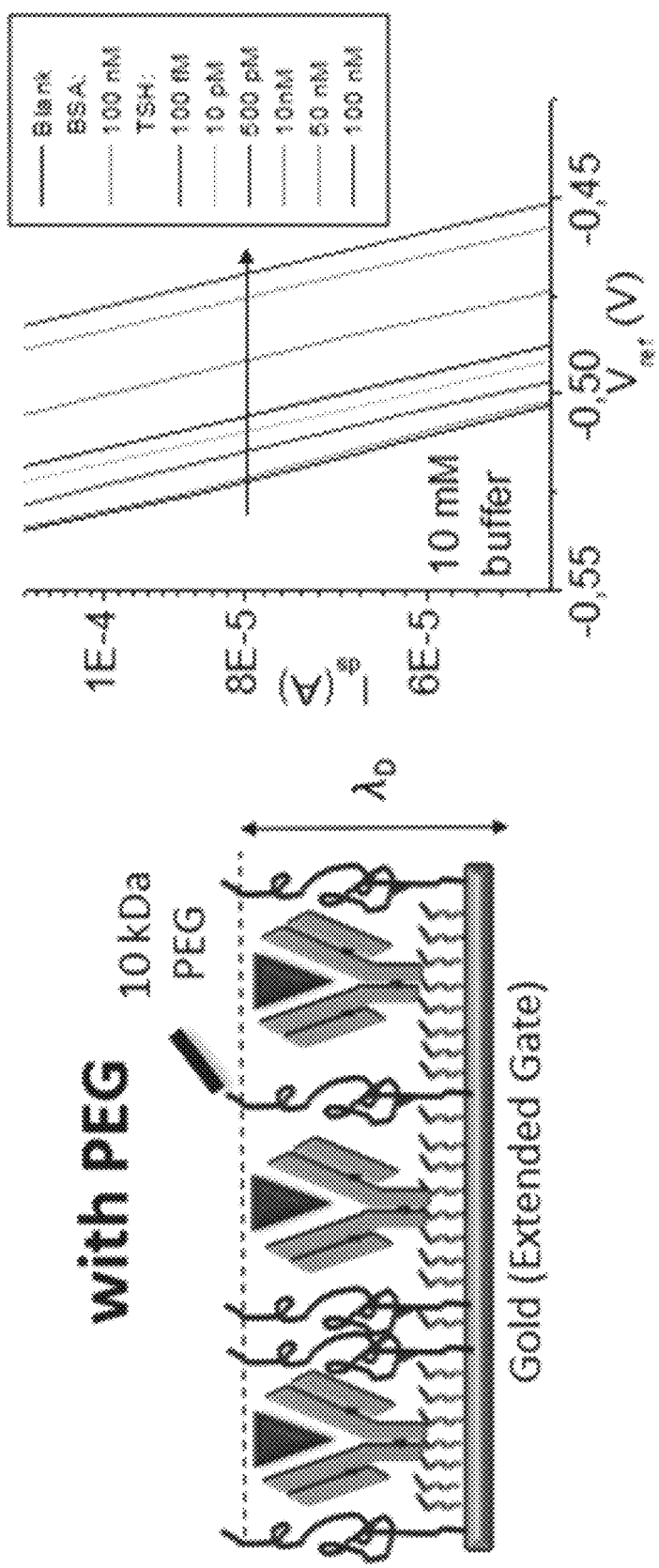
FIGS. 6A-6F show two different surface modifications on gold were compared, with (FIG. 6A) and without 10 kDa PEG (FIG. 6D). Both surfaces were functionalized with anti-TSH antibody fragments using short 0.5 kDa PEG linkers. The transistor transfer curves for different BSA and TSH concentrations in 10 mM buffer are plotted in (FIG. 6B) and (FIG. 6E) for the surface with PEG and without, respectively. The measured voltage shifts are shown in (FIG. 6C) for the surface with PEG and in (FIG. 6F) for the surface without PEG. The shifts are plotted vs. concentration of TSH (filled symbols) or BSA (open symbols) in 10 mM (triangles) and 150 mM buffer (squares). A clear signal enhancement is observed with PEG, with a significant response even in 150 mM buffer. The contribution of non-specific adsorption of BSA is small in all cases.
Figure 6D:
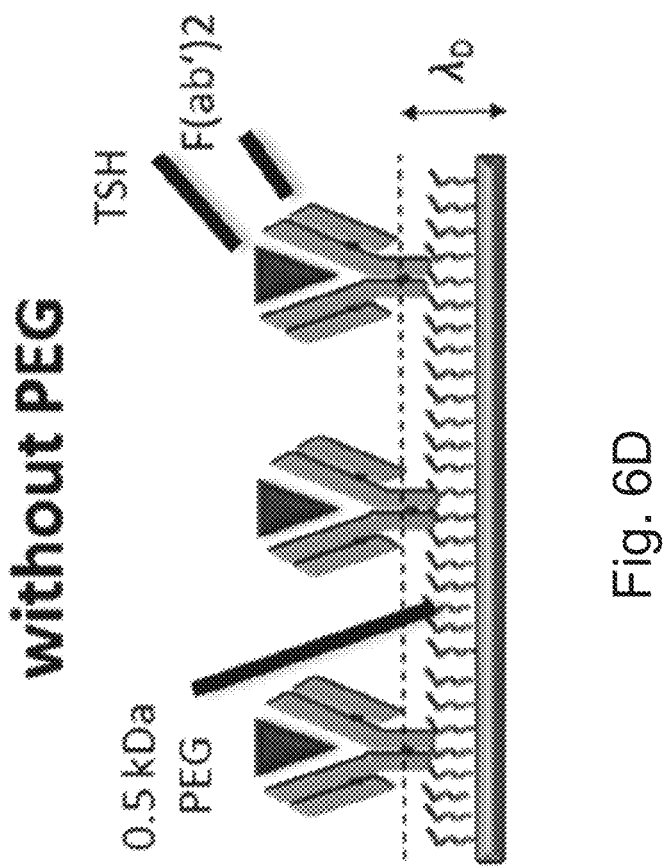
Figure 6C:
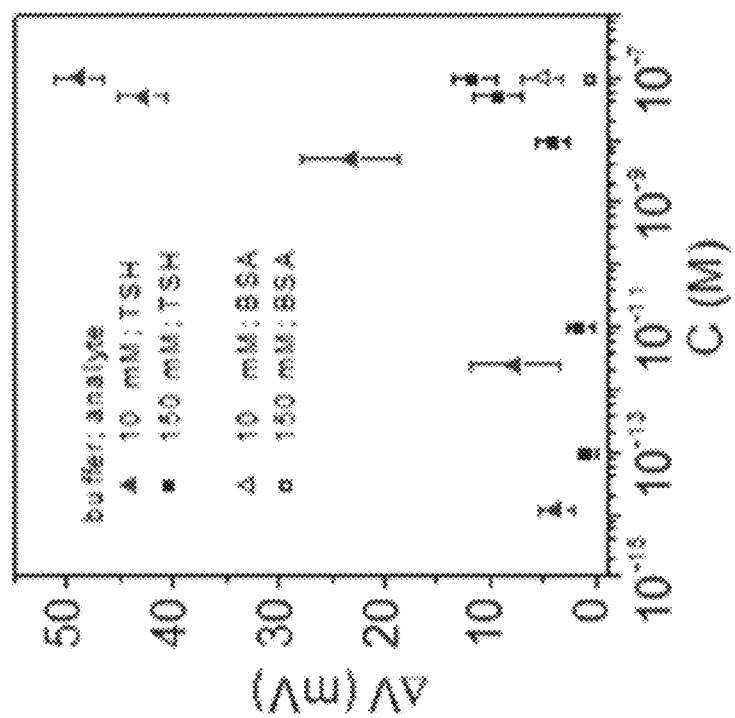
Figure 6F:
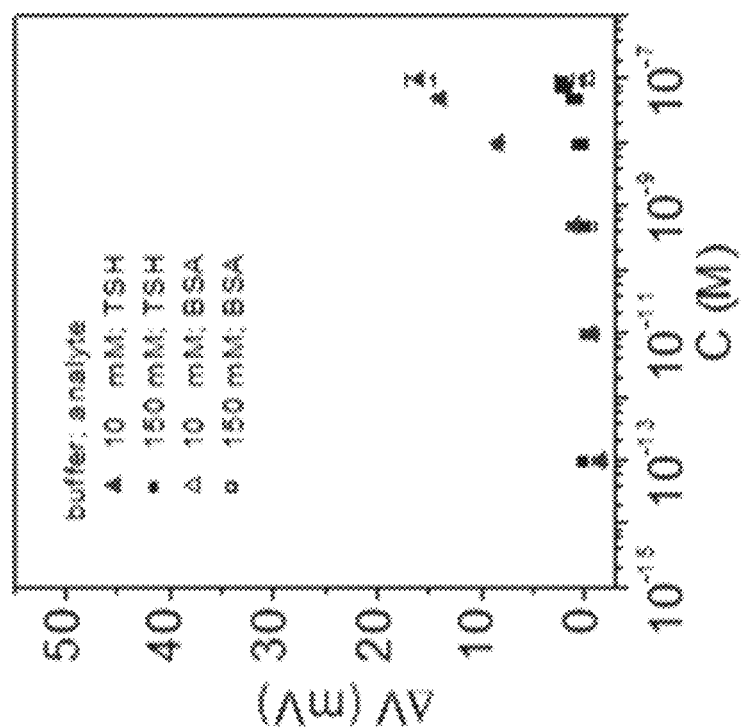
Figure 6E:
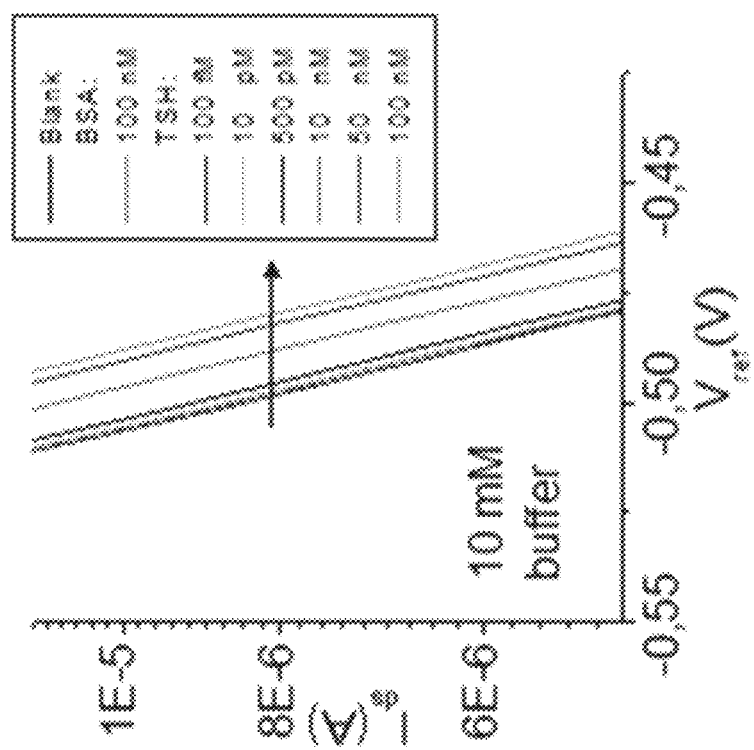

GFP-specific VHH was amino coupled to the carbon nanotubes using pyrene butyric acid (PBA) as a linker molecule. To study the effect of PEG on the signal, VHH was immobilized on both the PBA+PEG coated surface (FIG. 5A) and on the control CNT samples modified with PBA only (FIG. 5D). Both sensor surfaces were then exposed to various GFP concentrations dissolved in either 1 mM or 100 mM Tris buffer. The measurements are shown in FIGS. 5B, 5C for the PEGylated surface and in FIGS. 5E, 5F for the non-PEGylated surface. In both cases, the transfer curves shift to more positive values in response to increasing GFP concentration, with the PEGylated surface reacting more strongly (FIGS. 5B, 5E). FIGS. 5C and 5F compare the response of both sensors as a function of GFP concentration. Importantly, the signal of the PEGylated sensor exhibits a threefold enhancement in 100 mM buffer compared to the non-PEGylated surface (25 mV vs. 8 mV for 100 nM GFP). The observed signal enhancement in 1 mM buffer is less drastic and amounts to an approximately twofold increase (47 mV vs. 25 mV for 100 nM GFP). These results clearly indicate that the PEG has a strong positive impact on the maximum achievable sensor response.

Example 3: Transistor-Based Detection of Thyroid-Stimulating Hormone in Serum

Here, the surface chemistry approach combines antibody fragments as short biological receptors with desalting polyethylene glycol (PEG) molecules to enable direct label-free selective immunodetection in serum. Thyroid-stimulating hormone (TSH) is chosen here as a representative analyte—a relevant and well-characterized immuno sensing parameter with demanding sensitivity requirements. This approach is demonstrated with an extended-gate configuration, consisting of a gold sensing surface which is electrically connected to a commercial MOSFET transducer. This setup has the advantage of a simple chip fabrication and established thiol-gold chemistry for attachment of linker molecules. To evaluate the effect of desalting PEG on the Debye length, two different surface modifications are compared, with and without the addition of 10 kDa PEG. The sensing surface without Self-Assembled Monolayer (SAM) of SH-PEG-COOH (0.5 kDa), in the following referred to as the "Mono SAM" configuration. To study a system in presence of PEG the SH-PEG-COOH (0.5 kDa) and SH-PEG (10 kDa) are combined, named "Mix SAM" configuration (FIG. 6).

Figure 7:
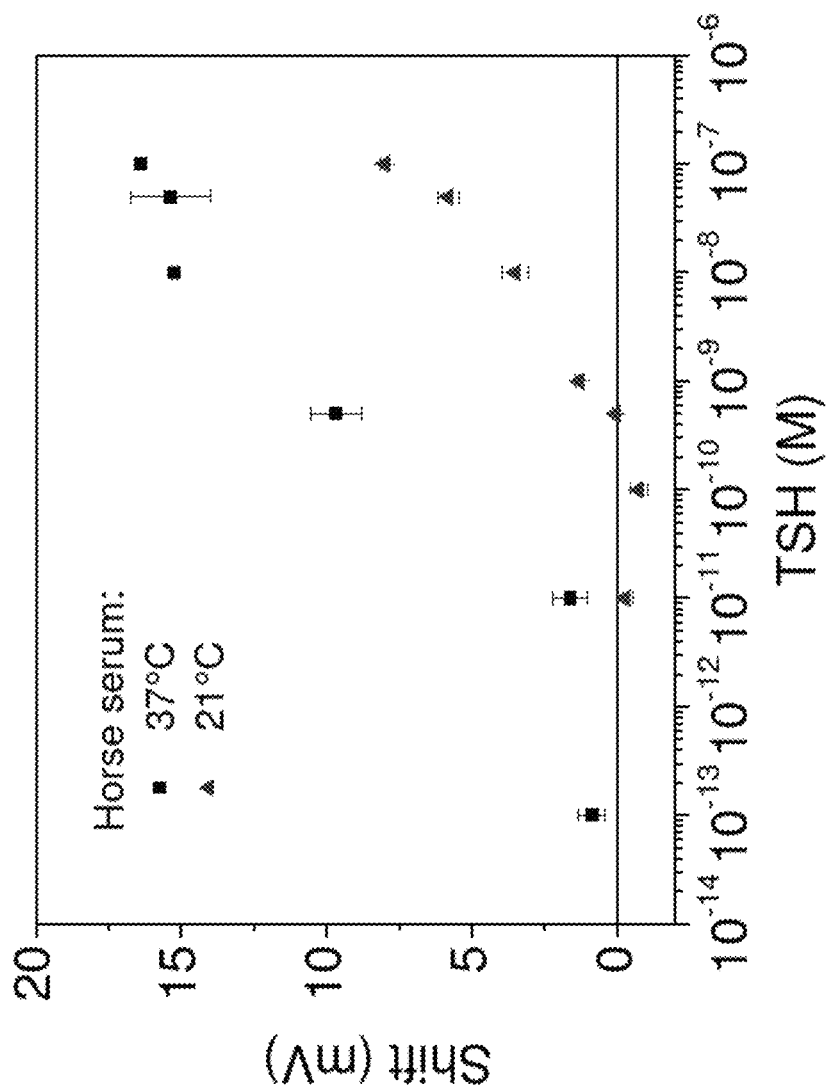
FIG. 7 shows TSH calibration curves measured in horse serum at 21° C. and 37° C. Error bars represent the standard deviation from 4 different chips.

Anti-TSH antibody fragments (F(ab')2) were immobilized on the sensor surface, and TSH detection in buffer and serum was demonstrated. PEG was co-immobilized on the surface to increase the Debye length. The PEG to linker ratio had been chosen as 1:20 to incorporate the fragments. With this ratio, a threefold signal enhancement was achieved in high ionic strength buffer, compared to a control surface without PEG (FIG. 6). Furthermore, the non-specific adsorption was tested by exposing the chips to BSA and was shown to be very low (<10% of the specific signal, FIG. 6). The measurements were then repeated in serum with at least 3 devices. The calibration curves are presented in FIG. 7. A strong signal enhancement was achieved if the measurements were performed at 37° C., leading to 3 orders of magnitude lower detection limit compared to 21° C. This improvement is mainly attributed to faster kinetics of the binding at higher temperature.

What is claimed is:

1. A method for manufacturing a functionalized surface on an electrode comprising the steps of:
   a) applying to the electrode a linker and at least one polymer capable of mediating a salting-out effect as a homogenous solution under conditions which allow for covalent or non-covalent immobilization of the linker and the at least one polymer capable of mediating a salting-out effect on the surface of the electrode, wherein the linker has the following structure:

A-B—C wherein A is a first functional group selected from the group consisting of thiol, silane, phosphonic acid, aromatic molecules, carboxyl, amine, NHS ester, and maleimide, wherein B is a low molecular weight (MW) polymer having a MW of 0.1 to 1 kDa, and wherein C is a second functional group selected from the group consisting of carboxyl, amine, NHS ester, and maleimide; and
   b) applying at least one detection agent to the electrode upon immobilization of the linker and the at least one polymer capable of mediating a salting-out effect under conditions which allow for covalent or non-covalent attachment of the at least one detection agent to the electrode via the immobilized linker; and wherein the conditions allow for distributing the at least one polymer capable of mediating a salting-out effect and the at least one detection agent on the surface of the electrode such that the at least one detection agent is present in equal amounts per surface area throughout the electrode surface and the at least one polymer capable of mediating a salting-out effect is arranged around the detection agent present in an amount
  i) allowing the reduction of ionic strength of a fluid sample in proximity to the detection agent, and
  ii) allowing for binding an analyte comprised in the fluid sample;
wherein the at least one polymer capable of mediating a salting-out effect has a molecular weight (MW) between 1 and 50 kDa and the size of the polymer capable of mediating a salting-out effect is larger or equal to the size of the at least one detection agent;
wherein the at least one polymer capable of mediating a salting-out effect is of the same class of polymers as B of the linker; and
wherein B of the linker and the at least one polymer capable of mediating a salting-out effect are selected from the group consisting of poly(ethylene glycol) (PEG), poly(ethylene oxide), poly(propylene glycol), polyglycerol, polyacrylamide (PAM), polyethyleneimine (PEI), polymethacrylate, poly(vinyl alcohol) (PVA), poly(vinylpyrrolidone) (PVP), and copolymers of the aforementioned polymers.

2. The method of claim 1, wherein the aromatic molecules of A include pyrene.

3. A method for manufacturing a functionalized surface on an electrode comprising the steps of:
  a) applying to the electrode a linker and at least one polymer capable of mediating a salting-out effect as a homogenous solution under conditions which allow for covalent or non-covalent immobilization of the linker and the at least one polymer capable of mediating a salting-out effect on the surface of the electrode, wherein the linker has the following structure:

wherein A is a first functional group selected from the group consisting of thiol, silane, phosphonic acid, aromatic molecules, carboxyl, amine, NHS ester, and maleimide, wherein B is a low molecular weight (MW) polymer having a MW of between 0.1 to 1 kDa, and
wherein C is a second functional group selected from the group consisting of carboxyl, amine, NHS ester, and maleimide; and wherein the molar weight ratio of the at least one polymer capable of mediating a salting-out effect to the linker, based on the molar ratio of the homogenous solution, is in the range of from 1:10 to 1:50; and
  b) applying at least one detection agent to the electrode upon immobilization of the linker and the at least one polymer capable of mediating a salting-out effect under conditions which allow for covalent or non-covalent attachment of the at least one detection agent to the electrode via the immobilized linker; and
wherein the conditions allow for distributing the at least one polymer capable of mediating a salting-out effect and the at least one detection agent on the surface of the electrode such that the at least one detection agent is present in equal amounts per surface area throughout the electrode surface and the at least one polymer capable of mediating a salting-out effect is arranged around the detection agent present in an amount
  i) allowing the reduction of ionic strength of a fluid sample in proximity to the detection agent, and
  ii) allowing for binding an analyte comprised in the fluid sample;
wherein the at least one polymer capable of mediating a salting-out effect has a molecular weight (MW) between 1 and 50 and the size of the polymer capable of mediating a salting-out effect is larger or equal to the size of the at least one detection agent;
wherein the at least one polymer capable of mediating a salting-out effect is of the same class of polymers as B of the linker; and
wherein B of the linker and the at least one polymer capable of mediating a salting-out effect are selected from the group consisting of poly(ethylene glycol) (PEG), poly(ethylene oxide), poly(propylene glycol), polyglycerol, polyacrylamide (PAM), polyethyleneimine (PEI), polymethacrylate, poly(vinyl alcohol) (PVA), poly(vinylpyrrolidone) (PVP), and copolymers of the aforementioned polymers.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
caatgcagat acactttttt                                              20

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
agtgtatctg cattg                                                   15
```